(12) United States Patent
Hansen et al.

(10) Patent No.: US 7,052,898 B2
(45) Date of Patent: May 30, 2006

(54) THERMOSTABLE ISOMERASE AND USE HEREOF, IN PARTICULAR FOR PRODUCING TAGATOSE

(75) Inventors: Ole C. Hansen, Værløse (DK); Flemming Jørgensen, Lyngby (DK); Peter Stougaard, Skibby (DK); Hans Bertelsen, Videbæk (DK); Karen Bøttcher, Kibæk (DK); Hans Jørgen Singel Christensen, Herning (DK); Kristian Eriknauer, Odder (DK)

(73) Assignee: Bioneer A/S (DK)

( * ) Notice: Subject to any disclaimer, the term of this patent is extended or adjusted under 35 U.S.C. 154(b) by 406 days.

(21) Appl. No.: 10/193,896

(22) Filed: Jul. 15, 2002

(65) Prior Publication Data

US 2003/0129710 A1 Jul. 10, 2003

Related U.S. Application Data

(60) Provisional application No. 60/386,209, filed on Jul. 16, 2001, and provisional application No. 60/305,155, filed on Jul. 16, 2001.

(51) Int. Cl.
*C12N 9/96* (2006.01)
*C12P 19/24* (2006.01)
*C12P 19/02* (2006.01)

(52) U.S. Cl. ............... 435/233; 435/94; 435/105

(58) Field of Classification Search ............... 435/233, 435/94, 105
See application file for complete search history.

(56) References Cited

U.S. PATENT DOCUMENTS 5,002,612 A  3/1991 Beadle et al.
6,057,135 A * 5/2000 Ibrahim et al. ............ 435/105

FOREIGN PATENT DOCUMENTS

WO   WO 00/68397 A1   11/2000
WO   WO 02/052021 A1   7/2002

OTHER PUBLICATIONS

Dische, Zacharias et al., "A New Spectrophotometric Method For The Detection and Determination of Keto Sugars and Trioses," *J. Biol. Chem*, vol. 192, pp. 583–587 (1951).

Heath, E.C. et al., "Pentose Fermentation by Lactobacillus Plantarum," *J. Biol. Chem.*, vol. 231, pp. 1031–1037 (1958).

Izumori, Ken et al., "Pentose Metabolism in *Mycobacterium smegmatis*: Comparison of L–Arabinose Isomerase Induced by L–Arabinose and D–Galactose," *J. Bacteriol.*, vol. 133, No. 1, pp. 413–414 (1978).

Larsen, Lise et al., "*Thermoanaerobacter Mathranii* sp. nov., an Ethanol–producing, Extremely Thermophilic Anaerobic Bacterium from a Hot Spring in Iceland," *Arch. Microbiol*, vol. 168, pp. 114–119 (1997).

Nakamatu, Tuyosi et al., "Crystallization and Properties of L–Arabinose Isomerase From *Lactobacillus Geyonil*," Biochim. Biophys. Acta. vol. 178, pp. 156–165 (1996).

Patrick, James W. et al., "Purification and Properties of an L–Arabinose Isomerase From *Escherichia coli*," J. Biol. Chem., vol. 243, No. 16, pp. 4312–4318 (1968).

Patrick, James W. et al., "Subunit Structure of L–Arabinose Isomerase from *Escherichia coli*," J. Biol. Chem., vol. 244, No. 16, pp. 4277–4283 (1969).

(Continued)

*Primary Examiner*—Charles L. Patterson, Jr.
(74) *Attorney, Agent, or Firm*—Finnegan, Henderson, Farabow, Garrett & Dunner, LLP

(57) ABSTRACT

A novel L-arabinose isomerase active enzyme and its corresponding gene, derived from a thermophilic source are provided. The enzyme is suitable for the production of D-tagatose, a useful low-calorie sweetener. The enzyme may be obtained from a *Thermoanaerobacter* species such as *Thermoanaerobacter mathranii*.

15 Claims, 8 Drawing Sheets

OTHER PUBLICATIONS

Figure 1:
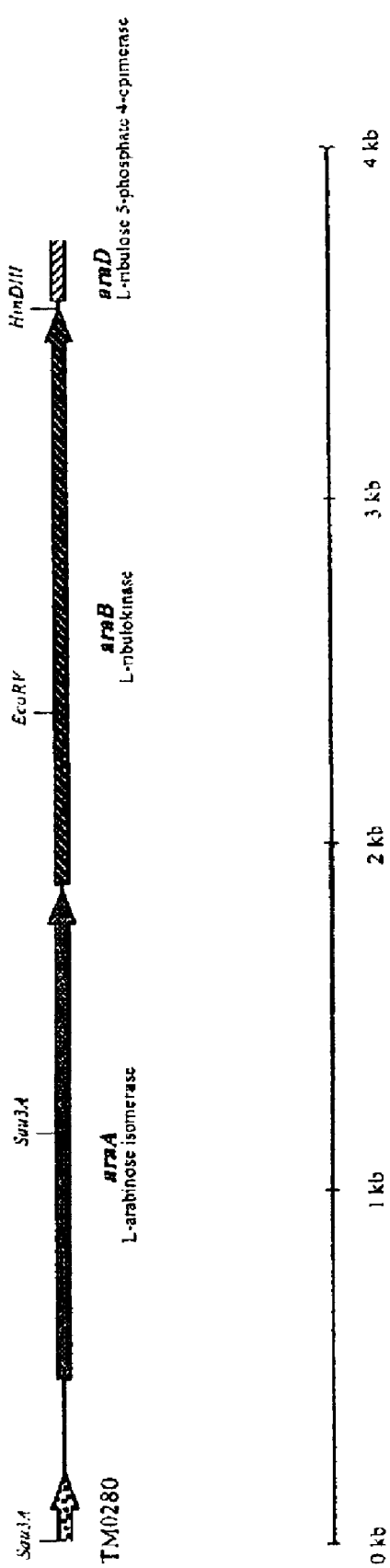

Sonne–Hansen, Jacob et al., "Xylanolytic Anaerobic Thermophiles From Icelandic Hot–Springs," Appl. Microbiol Biotechnology, vol. 38, pp. 537–541 (1993).

Thompson, Julie D., "The Clustal_X Windows Interface: Flexible Strategies for Multiple Sequence Alignment Aided by Quality Analysis Tools," Nuc. Acids Res., vol. 25, No. 24, pp. 4876–4882 (1997).

Yamanaka, K. et al., "L–Arabinose Isomerase," Methods in Emyrology, vol. IX, pp. 596–602 (1966).

F.M. Pisani et al., "Thermostable β–galactosidase from the archaebacterium *Sulfolobus solfataricus* Purification and properties," (1990) *Eur J Biochem*. 187:321–328.

Marco Moracci et al., "β–Glycosidase from *Sulfolobus solfataricus*," (2001) *Methods in Enzymology* 330:201–15.

Joachim E. Seemann et al., "Structure and Mechanism of L–Fucose Isomerase form *Escherichia coli*," *J. Mol. Biol.* 273:256–68, (1992).

Stephen F. Altschul et al., "*Basic Local Alignment Search Tool*,". J. Mol. Biol. 215:403–10 (1990).

* cited by examiner

| % identity pairwise between L-arabinose isomerase amino acid sequences | Thermoanaerobacter mathranii | Bacillus subtilis (Z75208) | Bacillus stearothermophilus (AF160811) | Bacillus halodurans (AP001513) | Thermotoga maritima (AE001709) | Escherichia coli (M11047) | Salmonella typhimurium (M11047) | Mycobacterium smegmatis (AB036736) |
|---|---|---|---|---|---|---|---|---|
| Thermoanaerobacter mathranii | - | 29 | 28 | 27 | 30 | 27 | 27 | 24 |
| Bacillus subtilis (Z75208) | | - | 64 | 61 | 55 | 52 | 52 | 49 |
| Bacillus stearothermophilus (AF160811) | | | - | 68 | 63 | 60 | 59 | 55 |
| Bacillus halodurans (AP001513) | | | | - | 59 | 57 | 55 | 50 |
| Thermotoga maritima (AE001709) | | | | | - | 55 | 56 | 50 |
| Escherichia coli (M15263) | | | | | | - | 95 | 49 |
| Salmonella typhimurium (M11047) | | | | | | | - | 49 |
| Mycobacterium smegmatis (AB036736) | | | | | | | | - |

Fig 2

Fig. 4a

```
E.coli          RLMQQGYGPAGEGDWKTAALLRIMKVMSTGLQGGTSFMEDYTYHFEKGNDLVLGSHMLEV
S.typhimurium   RLMQQGYGFAGEGDWKTAALLRIMKVMSTGLQGGTSFMEDYTYHPEKGNDLVLGSHMLEV
Y.pestis        RLMQQGYGFGGEGDWKTAALLRILKVMGTGLKGGTSFMEDYTYNFQPGNOLVVGSHMLEV
B.stearotherm   RLMAEGYGFGGEGDWKTAALVRLMKVMADGK--GTSFMEDYTYHLEPGNEMILGAHMLEV
B.halodurans    RLMAEGYGFGGEGDWKTAALLRMMKIIADGK--GTSFMEDYTYHLAEGNELVLGSHMLEI
B.subtilis      RLMEEKGYGFAGEGDWKTAALVRMMKIMAKGK--RTSFMEDYTYMPEPGNEMILGSHMLEV
C.aceto7646     RLMAEGYGFAGEGDWKTAALDRLLKVMTNNT--ATGFMEDYTYELSRGNEKALGAHHMLEV
C.aceto7645     RLMAEGYGFAGEGDWKTAALWRLFKIMTDNK--KTGFMEDYTYELSAGNERILGAHMLEV
T.maritima      RLMSEGYGFGAEGDWKAAGLVRAIKVMGTSLPGGTSFMEDYTYRLTPGNELVLGAHMLEV
T.neapol        RLMFEGYGFGAEGDWKAAGLVRALKVMGAGLPGGTSFMEDYTYMLTPGNELVLGAHMLEV
M.smegmatis     RLMADGFGFGAEGDWKTSAMVRTVKTMGVGLPGGTSFMEDYTYDLTPGSERILGAHMLEV
T.mathranii     WLMAEGYGYAAEGDAVTASLVAACHVLIG----OAHFTEMYAMDFKRNS--ILMSHMGEG
                .*  .*:*:..*** ::..:  ::    :  * *:: ..   .:** *
                289

E.coli          CPSIAVEEKPILDVQ-HLGIGGKDDPARLIFWTQTGPATVASLIDL-GDRYRLLVNCIDT
S.typhimurium   CPSIAVEEKPILDVQ-HLGIGGKEDPARLIFWTQTGPATVASLIDL-GDRYRLLVMCIDT
Y.pestis        CPSIAKEEKPLLDVQ-HLGIGGKADPARLIFSTPAGPALMASLIDM-GNRFRLLVNVVIT
B.stearotherm   CPTIAAT-RPRIEVM-PLSIGGREDPARLVFDGGEGAAVNASLIDL-GHRFRLIVMEVDA
B.halodurans    CPTIAAN-QPEIQVH-PLGICGREDPARLVFDGADGPALMASLIDL-GHRFRLVVNEVEA
B.subtilis      CPTVALD-QPKIEVH-SLSIGGREDPARLVFNGISGSATQASIVDI-LGHRFRLVLNEVNG
C.aceto7646     DPTFASD-KPKVIVK-PLGIGDKEDPARLIFWGSTGKGVAVSMLDL-GTHYRLIIWGLTA
C.aceto7645     DPTLAAS-RPRVVVK-PLGIGDKEAPARLIEDGVVGDGVVVSMLDL-CTHYRLLIWEVKA
T.maritima      CPTIAKE-KPRIEVH-PLSIGGRADPARLVPDGQEGPAVNASIVDM-GNRFRLVVHRVLS
T.neapol        CPTIAKE-KPRIEVH-PLSIGGKADPARLVFDGQEGPAVNASIVDM-GNRFRLVVHRVLS
M.smegmatis     CPSIAGQ-YPSLEVH-PLGIGMREDPVRLRFTAAPGSGVVLGICDM-GSRFHLVAHHVTV
T.mathranii     WWKIARKDRPIRLIDRELGIGKLDMPPTIVSMAQPGPATLVSLVSLEGERYRLVVSKGEI
                 .*        *:    *. *.*   *  :  *       .*  *   ::**.. 
                343

E.coli          VKTPHSLPRLPVANALWRAQPDLPTASEAWILAGGAHHTVFSRALWLNDNRQFAEMHDIE
S.typhimurium   VKTPHSLPKLPVRNALWRAQPDLPTASEAWILAGGAHHTVFSRALDLNDMRQFAEIHDIE
Y.pestis        VEQPHPLPKLPVARAIWQAQPSLATAAEAMIIAGGAHHTVFSQAVVGVDELRLYAFMHGIE
B.stearotherm   VKPEHDMPKLPVARTLWRPRPSLRDSAEAHILAGGARHTCFSFAVTTEQLQDFAEMAGIE
B.halodurans    IKPERDMPKLPVAKVLWKCKPSLSEATEAWIMAGGAHHTVFSFEVTPEQLYDMATLADIE
B.subtilis      QEIEKDMPHLPVARVLWKPEPSLKTAAEAWILAGGARHTCLSYELTAGGNLDMAEMAGIE
C.aceto7646     VKPDEDMPNLPVARNVWKPEPMFIEGVKSWIYAGGGHHTVVSLELTVEQVYDWSRMVGLE
C.aceto7645     VKPTEDAPHLPVAKLVHQPQPHEKDAVKAMIYAGGGHHTVATLELTVEQVYDWSKMVGLE
T.maritima      VPIERKMPKLPTARVLWRPLPDFKRATTAWILAGGSHHTAFSTAIDVEYLIDMAEALEIE
T.neapol        VPIERKMPKLPTARVLMKPLPDFKRATTAWILAGGSHHTAFSTAUDVEYLIDMAEALEIE
M.smegmatis     VEPSAPLPNLPVACAVWEPEPSWSTSTEAMLMAGGPHHTVLTTAVSPTTLDDFATITGTE
T.mathranii     LDT-EEARYIEMPYFHFRPSTGVKACLDGWLTMGCTHHKECLWLGDNTRRMKIICNLLDIE
                                  *:   **  .           .
                403

E.coli          ITVIDMDTRLPAFKDALRMNEVYYGFRR--
S.typhimurium   IAVIDHDTHLPAFKDALRMNEVYYGFKR--
Y.pestis        FLLIDNDTTLPAFKNEIRMNEVYYQLNR--
B.stearotherm   LVVINEHTSVSSFKNELKMNEVFWRGR---
B.halodurans    VVFINDKTDVLQFQQQLQRMEAFRRLFK-
B.subtilis      SVLISRDTTIHKLKHELKMNEALYRLQK--
C.aceto7646     AVIIDKDTKLRDIIEKTTK-----------
C.aceto7645     TIVIDHNTMLRDIIKETSR-----------
T.maritima      YVVIDEMLDLEDFKKELRMNELYMGLLKR-
T.neapol        YLVIDENLDLENFKKELRMNELYMGLLKR-
M.smegmatis     LLQIDQHTTPREFQREMRMMAVYHHIAAGL
T.mathranii     YVEV-------------------------
                :
                462
```

Fig. 4 b

SEQUENCE LISTING

```
<160> NUMBER OF SEQ ID NOS: 14

<210> SEQ ID NO 1
<211> LENGTH: 3719
<212> TYPE: DNA
<213> ORGANISM: Thermoanaerobacter matrahnii
<220> FEATURE:
<221> NAME/KEY: CDS
<222> LOCATION: (462)...(1860)
<223> OTHER INFORMATION: Open reading frame of araA gene

<400> SEQUENCE: 1
gatctattaa acggtgtgtg tgtaatagag acagaggcag aacgagaaga ttatgggtca        60
tggggagaag agctttataa ggtagatgtt aatgtatcgt ataagcccgt gagaataaaa       120
tttataccgt atttttgcatg ggcgaaccgt gcaccgggtg aaatgatggt atgggtaagg      180
gaaaagtaaa attactagaa ggggttttaa tgtgtttaat caagaaggta gaaatatagg      240
tttaaatggc aaaggaacaa gttttttgtat attgataaag tatataaaac ctaagatagt      300
tttatattta tttgtctaag ttttagaaat aaattttttta aaaacaaaga aggaattttg      360
aataaaatgt agaatatatt aattataaat gtacgtacat ctaatatcat gataattaaa      420
atatacgaac aacaaaataa caaatcaaag ggaggattta t tat gca aac caa gaa      476
                                                 Tyr Ala Asn Gln Glu
                                                   1               5 aaa gcc gca aat agg att ttt agg cat tat gca aga gtt gta cga tga        524
Lys Ala Ala Asn Arg Ile Phe Arg His Tyr Ala Arg Val Val Arg *
             10                  15                  20 tat gtt acc agg cat tac tga aag aca aga aaa ata tgc aag aga agt        572
Tyr Val Thr Arg His Tyr *   Lys Thr Arg Lys Ile Cys Lys Arg Ser
         25                      30                      35 tat aga aca act tca aga tgt tgc cga ttt tca ttt tcc taa agc agc        620
Tyr Arg Thr Thr Ser Arg Cys Cys Arg Phe Ser Phe Ser *   Ser Ser
         40                      45                      50
```

```
                                                      -continued aaa gaa tag aca gga cat tga aca tat tgt gaa aga att taa tga aaa    668
Lys Glu  *  Thr Gly His  *  Thr Tyr Cys Glu Arg Ile  *   *  Lys
                     55              60 aga cct tga tgg tat tat gat agt aat gct tac gta tgg acc tgc tac    716
Arg Pro  *  Trp Tyr Tyr Asp Ser Asn Ala Tyr Val Trp Thr Cys Tyr
             65              70              75 aaa tat tgt taa tgc act aag gaa taa taa act acc tat tat gct tgc    764
Lys Tyr Cys  *  Cys Thr Lys Glu  *   *  Thr Thr Tyr Tyr Ala Cys
         80              85                              90 gaa cat tca acc tgt tcc gac agt aac aga gga ttg gga tat ggg aga    812
Glu His Ser Thr Cys Ser Asp Ser Asn Arg Gly Leu Gly Tyr Gly Arg
                 95             100             105 ttt gac ata caa tca agg tgt tca cgg tgc cca aga tac agc aaa tgc    860
Phe Asp Ile Gln Ser Arg Cys Ser Arg Cys Pro Arg Tyr Ser Lys Cys
             110             115             120 cat ttt aag gat ggg aat taa gtg tcc tat tat tac aga aga atg gca    908
His Phe Lys Asp Gly Asn  *  Val Ser Tyr Tyr Tyr Arg Arg Met Ala
             125             130             135 ttc aga aga att taa aaa att tgt tgg aga ttg ggc taa agc tgt gca    956
Phe Arg Arg Ile  *  Lys Ile Cys Trp Arg Leu Gly  *  Ser Cys Ala
         140             145                     150 gac aat taa agc att gcg aaa cat gaa aat agc gca gtt tgg aag aat   1004
Asp Asn  *  Ser Ile Ala Lys His Glu Asn Ser Ala Val Trp Lys Asn
             155             160             165 gca tgg aat gta tga tat ttt ggg aga tga tgc agc ctt tac aag aaa   1052
Ala Trp Asn Val  *  Tyr Phe Gly Arg  *  Cys Ser Leu Tyr Lys Lys
             170             175             180 aat agg tcc gca aat taa tca aga ata cat tgg cga agt tta tag ata   1100
Asn Arg Ser Ala Asn  *  Ser Arg Ile His Trp Arg Ser Leu  *  Ile
             185             190 tat gga aac tgc gac aga aga gga gat taa tgc ggt tat tga aga gaa   1148
Tyr Gly Asn Cys Asp Arg Arg Gly Asp  *  Cys Gly Tyr  *  Arg Glu
195             200             205 tag aaa gaa ttt tta tat cga tcc aaa tct tag cga aga aag cca tag   1196
 *  Lys Glu Phe Leu Tyr Arg Ser Lys Ser  *  Arg Arg Lys Pro  *
         210             215             220 ata tgc tgc aag att aca aat tgg att taa aaa att tct tat taa taa   1244
Ile Cys Cys Lys Ile Thr Asn Trp Ile  *  Lys Ile Ser Tyr  *   *
             225             230 agg ata tga cgg att tac tgc gca ttt cga tgt gtt taa agg aga tgg   1292
Arg Ile  *  Arg Ile Tyr Cys Ala Phe Arg Cys Val  *  Arg Arg Trp
235         240             245 aag att caa gca aat tcc aat gat ggc tgc gtc aaa ttt aat ggc tga   1340
Lys Ile Gln Ala Asn Ser Asn Asp Gly Cys Val Lys Phe Asn Gly  *
         250             255             260 agg ata tgg ata tgc agc aga ggg tga tgc tgt aac tgc aag ttt ggt   1388
Arg Ile Trp Ile Cys Ser Arg Gly  *  Cys Cys Asn Cys Lys Phe Gly
         265             270             275 tgc ggc agg tca tgt att gat agg aga tgc aca ttt tac tga gat gta   1436
Cys Gly Arg Ser Cys Ile Asp Arg Arg Cys Thr Phe Tyr  *  Asp Val
         280             285             290 cgc tat gga ttt taa gag aaa ttc aat ttt aat gag cca tat ggg cga   1484
Arg Tyr Gly Phe  *  Glu Lys Phe Asn Phe Asn Glu Pro Tyr Gly Arg
         295             300             305 agg taa ctg gaa aat agc aag aaa gga tag acc gat taa act tat tga   1532
Arg  *  Leu Glu Asn Ser Lys Lys Gly  *  Thr Asp  *  Thr Tyr  *
         310             315             320 tag aga act ggg cat tgg aaa act tga taa tcc gcc gac aat tgt gtt   1580
 *  Arg Thr Gly His Trp Lys Thr  *   *  Ser Ala Asp Asn Cys Val
```

|  |  |  |  |  |  |  |  |  |  |  |  |  |  |  |  |
|---|---|---|---|---|---|---|---|---|---|---|---|---|---|---|---|
|  |  |  |  | 325 |  |  |  |  |  | 330 |  |  |  |  |  |
| tat | ggc | aca | acc | tgg | gcc | agc | aac | tct | tgt | ttc | ttt | agt | atc | ctt | aga | 1628 |
| Tyr | Gly | Thr | Thr | Trp | Ala | Ser | Asn | Ser | Cys | Phe | Phe | Ser | Ile | Leu | Arg |
|  | 335 |  |  |  | 340 |  |  |  |  | 345 |  |  |  |  |  |
| agg | aga | aag | ata | tag | gtt | agt | tgt | gtc | aaa | agg | aga | aat | tct | gga | tac | 1676 |
| Arg | Arg | Lys | Ile | * | Val | Ser | Cys | Val | Lys | Arg | Arg | Asn | Ser | Gly | Tyr |
| 350 |  |  |  |  | 355 |  |  |  |  | 360 |  |  |  |  |  |
| aga | aga | agc | aaa | gta | tat | tga | aat | gcc | ata | ttt | cca | ctt | tag | acc | ttc | 1724 |
| Arg | Arg | Ser | Lys | Val | Tyr | * | Asn | Ala | Ile | Phe | Pro | Leu | * | Thr | Phe |
| 365 |  |  |  | 370 |  |  |  |  | 375 |  |  |  |  |  |  |
| aac | agg | tgt | gaa | ggc | atg | tct | tga | tgg | atg | gct | tac | aaa | tgg | agg | aac | 1772 |
| Asn | Arg | Cys | Glu | Gly | Met | Ser | * | Trp | Met | Ala | Tyr | Lys | Trp | Arg | Asn |
|  | 380 |  |  |  | 385 |  |  |  |  | 390 |  |  |  |  |  |
| aca | tca | tga | atg | ttt | aaa | tct | agg | tga | taa | cac | acg | gag | atg | gaa | aat | 1820 |
| Thr | Ser | * | Met | Phe | Lys | Ser | Arg | * | * | His | Thr | Glu | Met | Glu | Asn |
|  | 395 |  |  |  | 400 |  |  |  |  | 405 |  |  |  |  |  |
| att | atg | taa | cct | ctt | gga | cat | tga | ata | tgt | aga | agt | ata | g | ggggatgaaa |  | 1870 |
| Ile | Met | * | Pro | Leu | Gly | His | * | Ile | Cys | Arg | Ser | Ile |
|  |  |  |  | 410 |  |  |  |  | 415 |

```
aatggcaaag tattcaattg gaatagatta cgggacagag tctgcaaggg ctctgctcct    1930
taatcttgag acgggagaag aagtagctac ttctgtaatg aattatcccc atggcgtgat    1990
ggatgaagaa cttcctgatg gaacaaaact tccacaagat tgggcattac aacatccaga    2050
tgactatatt gaagttttaa agaaaatagt acctgatgta ataaatcagg caggtataga    2110
caaagctgat gtaataggct taggcataga ttttacagct tgtactatgt tgcctataaa    2170
aaaagatgga actcctcttt gtgacatccc ccagtacaaa tcgaaccctc attcatatgt    2230
taagttatgg aaacatcatg ctgcgcaacc tgaagcaaac aaattgaatg aaatagcatc    2290
acaagggggt gaggattttt tagcaaggta tggaggaaaa atatcttcag aatggctcat    2350
acccaaaata tggcaaatat taaatgaagc gccagatatc tatgaagaag ctgataaatt    2410
tattgaagct actgattggg ttgttatgaa gctaacaggt aatgaaaggc gaaatagctg    2470
tactgcaggc tataaagcga tttggcacaa aagaaagggg tatccttcca agatttctt    2530
tcgagcatta gatgagaggc ttgaaaattt ggtagaagaa aaattatcta aagatatata    2590
tccattaggt acaaaagcag gggaattgac gcctgaaatg gcaaaaataa tgggcttaaa    2650
cccgggagta gcggttgctg taggcaatgt tgatgctcat gtttcagtac cagcagtagg    2710
agttacatcg ccagggaaaa tggtaatggt aatgggaact tcgatttgcc atttggtgtt    2770
agatgataaa gaagtagagg tcccaggcat gtgtggcgtt gtagaagatg gaattatacc    2830
aggcttttat ggatatgaag caggacaatc tgcggttggc gacatctttg cctggtttgt    2890
tgataattgt gtgccgtacg aatacaaaat tgaagcagaa aaaagaggga taagtattca    2950
cgagttatta acagaaaaag ccgcaaagct aaaacccgga gaaagtggcc tcttggcgat    3010
tgactggtgg aacggaaaca ggtcagtact agtagatgca gaccttactg gtgtaatatt    3070
aggaatgact ttaactacga aacctgagga gatatacaga gcattaatcg aagcaacagc    3130
ttttgggacg aggatgataa ttgatacttt taatcaaaat ggagtaagta ttagtgaact    3190
gtacgcttgt ggaggacttc ctgaaaaaaa tcctatgctt atgcaaatct atgctgatgt    3250
tacaaatctc gaaattaaag tatcaaaatc ttcacaaaca ccagcacttg gtgcagcaat    3310
gtttggagca gttgcagcag gtaaagcaaa aggagggttt gatagtatat ttgaagcggc    3370
acgagtaata cccaagctaa aggaagaaac atacaatcca atacctgaaa atgttgaaat    3430
atatgataaa ttatttgaag aatacaaaact tcttcatgac tattttggca gaggtataaa    3490
```

-continued

```
taatgtaatg aaaaggctaa aagccttaaa agaggggtt tccaatgtta gagaagctta    3550
aagaacgagt atacaaaatg aatatgatgt tgccgaaaaa taatcttgtt acaatgacaa    3610
gtgggaatgt cagtggaaga gatgttgaaa caggatatgt agttataaaa ccaagcggga    3670
ttccttatga agaaatgcaa ccagaggata tggttgtggt tgaccttaa               3719
```

<210> SEQ ID NO 2
<211> LENGTH: 465
<212> TYPE: PRT
<213> ORGANISM: Thermoanaerobacter matrahnii, araA sequence

<400> SEQUENCE: 2

```
Met Gln Thr Lys Lys Pro Gln Ile Gly Phe Leu Gly Ile Met Gln
  1               5                  10                  15

Glu Leu Tyr Asp Asp Met Leu Pro Gly Ile Thr Glu Arg Gln Glu Lys
                 20                  25                  30

Tyr Ala Arg Glu Val Ile Glu Gln Leu Gln Asp Val Ala Asp Phe His
             35                  40                  45

Phe Pro Lys Ala Ala Lys Asn Arg Gln Asp Ile Glu His Ile Val Lys
         50                  55                  60

Glu Phe Asn Glu Lys Asp Leu Asp Gly Ile Met Ile Val Met Leu Thr
 65                  70                  75                  80

Tyr Gly Pro Ala Thr Asn Ile Val Asn Ala Leu Arg Asn Asn Lys Leu
                 85                  90                  95

Pro Ile Met Leu Ala Asn Ile Gln Pro Val Pro Thr Val Thr Glu Asp
            100                 105                 110

Trp Asp Met Gly Asp Leu Thr Tyr Asn Gln Gly Val His Gly Ala Gln
            115                 120                 125

Asp Thr Ala Asn Ala Ile Leu Arg Met Gly Ile Lys Cys Pro Ile Ile
        130                 135                 140

Thr Glu Glu Trp His Ser Glu Glu Phe Lys Lys Phe Val Gly Asp Trp
145                 150                 155                 160

Ala Lys Ala Val Gln Thr Ile Lys Ala Leu Arg Asn Met Lys Ile Ala
                165                 170                 175

Gln Phe Gly Arg Met His Gly Met Tyr Asp Ile Leu Gly Asp Asp Ala
            180                 185                 190

Ala Phe Thr Arg Lys Ile Gly Pro Gln Ile Asn Gln Glu Tyr Ile Gly
        195                 200                 205

Glu Val Tyr Arg Tyr Met Glu Thr Ala Thr Glu Glu Ile Asn Ala
            210                 215                 220

Val Ile Glu Glu Asn Arg Lys Asn Phe Tyr Ile Asp Pro Asn Leu Ser
225                 230                 235                 240

Glu Glu Ser His Arg Tyr Ala Ala Arg Leu Gln Ile Gly Phe Lys Lys
                245                 250                 255

Phe Leu Ile Asn Lys Gly Tyr Asp Gly Phe Thr Ala His Phe Asp Val
            260                 265                 270

Phe Lys Gly Asp Gly Arg Phe Lys Gln Ile Pro Met Met Ala Ala Ser
        275                 280                 285

Asn Leu Met Ala Glu Gly Tyr Gly Tyr Ala Ala Glu Gly Asp Ala Val
            290                 295                 300

Thr Ala Ser Leu Val Ala Ala Gly His Val Leu Ile Gly Asp Ala His
305                 310                 315                 320

Phe Thr Glu Met Tyr Ala Met Asp Phe Lys Arg Asn Ser Ile Leu Met
                325                 330                 335
```

```
Ser His Met Gly Glu Gly Asn Trp Lys Ile Ala Arg Lys Asp Arg Pro
            340                 345                 350

Ile Lys Leu Ile Asp Arg Glu Leu Gly Ile Gly Lys Leu Asp Asn Pro
            355                 360                 365

Pro Thr Ile Val Phe Met Ala Gln Pro Gly Pro Ala Thr Leu Val Ser
            370                 375                 380

Leu Val Ser Leu Glu Gly Glu Arg Tyr Arg Leu Val Val Ser Lys Gly
385                 390                 395                 400

Glu Ile Leu Asp Thr Glu Ala Lys Tyr Ile Glu Met Pro Tyr Phe
            405                 410                 415

His Phe Arg Pro Ser Thr Gly Val Lys Ala Cys Leu Asp Gly Trp Leu
            420                 425                 430

Thr Asn Gly Gly Thr His His Glu Cys Leu Asn Leu Gly Asp Asn Thr
            435                 440                 445

Arg Arg Trp Lys Ile Leu Cys Asn Leu Leu Asp Ile Glu Tyr Val Glu
450                 455                 460

Val
465

<210> SEQ ID NO 3
<211> LENGTH: 500
<212> TYPE: PRT
<213> ORGANISM: E.coli

<400> SEQUENCE: 3

Met Thr Ile Phe Asp Asn Tyr Glu Val Trp Phe Val Ile Gly Ser Gln
1               5                   10                  15

His Leu Tyr Gly Pro Glu Thr Leu Arg Gln Val Thr Gln His Ala Glu
            20                  25                  30

His Val Val Asn Ala Leu Asn Thr Glu Ala Lys Leu Pro Cys Lys Leu
            35                  40                  45

Val Leu Lys Pro Leu Gly Thr Thr Pro Asp Glu Ile Thr Ala Ile Cys
    50                  55                  60

Arg Asp Ala Asn Tyr Asp Asp Arg Cys Ala Gly Leu Val Val Trp Leu
65                  70                  75                  80

His Thr Phe Ser Pro Ala Lys Met Trp Ile Asn Gly Leu Thr Met Leu
            85                  90                  95

Asn Lys Pro Leu Leu Gln Phe His Thr Gln Phe Asn Ala Ala Leu Pro
            100                 105                 110

Trp Asp Ser Ile Asp Met Asp Phe Met Asn Leu Asn Gln Thr Ala His
            115                 120                 125

Gly Gly Arg Glu Phe Gly Phe Ile Gly Ala Arg Met Arg Gln Gln His
            130                 135                 140

Ala Val Val Thr Gly His Trp Gln Asp Lys Gln Ala His Glu Arg Ile
145                 150                 155                 160

Gly Ser Trp Met Arg Gln Ala Val Ser Lys Gln Asp Thr Arg His Leu
            165                 170                 175

Lys Val Cys Arg Phe Gly Asp Asn Met Arg Glu Val Ala Val Thr Asp
            180                 185                 190

Gly Asp Lys Val Ala Ala Gln Ile Lys Phe Gly Phe Ser Val Asn Thr
            195                 200                 205

Trp Ala Val Gly Asp Leu Val Gln Val Val Asn Ser Ile Ser Asp Gly
    210                 215                 220

Asp Val Asn Ala Leu Val Asp Glu Tyr Glu Ser Cys Tyr Thr Met Thr
```

-continued

```
            225                 230                 235                 240
Pro Ala Thr Gln Ile His Gly Glu Lys Arg Gln Asn Val Leu Glu Ala
                245                 250                 255
Ala Arg Ile Glu Leu Gly Met Lys Arg Phe Leu Glu Gln Gly Gly Phe
            260                 265                 270
His Ala Phe Thr Thr Thr Phe Glu Asp Leu His Gly Leu Lys Gln Leu
            275                 280                 285
Pro Gly Leu Ala Val Gln Arg Leu Met Gln Gly Tyr Gly Phe Ala
        290                 295                 300
Gly Glu Gly Asp Trp Lys Thr Ala Ala Leu Leu Arg Ile Met Lys Val
305                 310                 315                 320
Met Ser Thr Gly Leu Gln Gly Gly Thr Ser Phe Met Glu Asp Tyr Thr
                325                 330                 335
Tyr His Phe Glu Lys Gly Asn Asp Leu Val Leu Gly Ser His Met Leu
            340                 345                 350
Glu Val Cys Pro Ser Ile Ala Val Glu Glu Lys Pro Ile Leu Asp Val
            355                 360                 365
Gln His Leu Gly Ile Gly Gly Lys Asp Asp Pro Ala Arg Leu Ile Phe
        370                 375                 380
Asn Thr Gln Thr Gly Pro Ala Ile Val Ala Ser Leu Ile Asp Leu Gly
385                 390                 395                 400
Asp Arg Tyr Arg Leu Leu Val Asn Cys Ile Asp Thr Val Lys Thr Pro
                405                 410                 415
His Ser Leu Pro Lys Leu Pro Val Ala Asn Ala Leu Trp Lys Ala Gln
            420                 425                 430
Pro Asp Leu Pro Thr Ala Ser Glu Ala Trp Ile Leu Ala Gly Gly Ala
            435                 440                 445
His His Thr Val Phe Ser His Ala Leu Asn Leu Asn Asp Met Arg Gln
        450                 455                 460
Phe Ala Glu Met His Asp Ile Glu Ile Thr Val Ile Asp Asn Asp Thr
465                 470                 475                 480
Arg Leu Pro Ala Phe Lys Asp Ala Leu Arg Trp Asn Glu Val Tyr Tyr
                485                 490                 495
Gly Phe Arg Arg
            500

<210> SEQ ID NO 4
<211> LENGTH: 500
<212> TYPE: PRT
<213> ORGANISM: S.typhimurium

<400> SEQUENCE: 4

Met Thr Ile Phe Asp Asn Tyr Glu Val Trp Phe Val Ile Gly Ser Gln
 1               5                  10                  15
His Leu Tyr Gly Ala Glu Thr Leu Arg Gln Val Thr Gln His Ala Glu
                20                  25                  30
His Val Val Asn Ala Leu Asn Thr Glu Ala Lys Leu Pro Cys Lys Leu
            35                  40                  45
Val Leu Lys Pro Leu Gly Thr Ser Pro Asp Glu Ile Thr Ala Ile Cys
        50                  55                  60
Arg Asp Ala Asn Tyr Asp Asp Arg Cys Ala Gly Leu Val Val Trp Leu
65                  70                  75                  80
His Thr Phe Ser Pro Ala Lys Met Trp Ile Asn Gly Leu Ser Ile Leu
                85                  90                  95
```

```
Asn Lys Pro Leu Leu Gln Phe His Thr Gln Phe Asn Ala Ala Leu Pro
        100                 105                 110
Trp Asp Ser Ile Asp Met Asp Phe Met Asn Leu Asn Gln Thr Ala His
            115                 120                 125
Gly Gly Arg Glu Phe Gly Phe Ile Gly Ala Arg Met Arg Gln Gln His
    130                 135                 140
Ala Val Val Thr Gly His Trp Gln Asp Lys Glu Ala His Thr Arg Ile
145                 150                 155                 160
Gly Ala Trp Met Arg Gln Ala Val Ser Lys Gln Asp Thr Arg Gln Leu
                165                 170                 175
Lys Val Cys Arg Phe Gly Asp Asn Met Arg Glu Val Ala Val Thr Asp
                180                 185                 190
Gly Asp Lys Val Ala Ala Gln Ile Lys Phe Gly Phe Ser Val Asn Thr
            195                 200                 205
Trp Ala Val Gly Asp Leu Val Gln Val Val Asn Ser Ile Gly Asp Gly
    210                 215                 220
Asp Ile Asn Ala Leu Ile Asp Glu Tyr Glu Ser Ser Tyr Thr Leu Thr
225                 230                 235                 240
Pro Ala Thr Gln Ile His Gly Asp Lys Arg Gln Asn Val Arg Glu Ala
                245                 250                 255
Ala Gly Ile Glu Leu Gly Met Lys Arg Phe Leu Glu Gln Gly Gly Phe
            260                 265                 270
His Ala Phe Thr Thr Thr Phe Glu Asp Leu His Gly Leu Lys Gln Leu
        275                 280                 285
Pro Gly Leu Ala Val Gln Arg Leu Met Gln Gln Gly Tyr Gly Phe Ala
    290                 295                 300
Gly Glu Gly Asp Trp Lys Thr Ala Ala Leu Leu Arg Ile Met Lys Val
305                 310                 315                 320
Met Ser Thr Gly Leu Gln Gly Gly Thr Ser Phe Met Glu Asp Tyr Thr
                325                 330                 335
Tyr His Phe Glu Lys Gly Asn Asp Leu Val Leu Gly Ser His Met Leu
            340                 345                 350
Glu Val Cys Pro Ser Ile Ala Val Glu Glu Lys Pro Ile Leu Asp Val
        355                 360                 365
Gln His Leu Gly Ile Gly Gly Lys Glu Asp Pro Ala Arg Leu Ile Phe
    370                 375                 380
Asn Thr Gln Thr Gly Pro Ala Ile Val Ala Ser Leu Ile Asp Leu Gly
385                 390                 395                 400
Asp Arg Tyr Arg Leu Leu Val Asn Cys Ile Asp Thr Val Lys Thr Pro
                405                 410                 415
His Ser Leu Pro Lys Leu Pro Val Arg Asn Ala Leu Trp Lys Ala Gln
            420                 425                 430
Pro Asp Leu Pro Thr Ala Ser Glu Ala Trp Ile Leu Ala Gly Gly Ala
        435                 440                 445
His His Thr Val Phe Ser His Ala Leu Asp Leu Asn Asp Met Arg Gln
    450                 455                 460
Phe Ala Glu Ile His Asp Ile Glu Ile Ala Val Ile Asp Asn Asp Thr
465                 470                 475                 480
His Leu Pro Ala Phe Lys Asp Ala Leu Arg Trp Asn Glu Val Tyr Tyr
                485                 490                 495
Gly Phe Lys Arg
            500
```

-continued

<210> SEQ ID NO 5
<211> LENGTH: 498
<212> TYPE: PRT
<213> ORGANISM: Y.pestis

<400> SEQUENCE: 5

```
Met Asp Val Phe Lys Gln Ser Glu Val Trp Phe Val Ile Gly Ser Gln
 1               5                  10                  15

Asn Leu Tyr Gly Pro Lys Thr Leu Gln Gln Val Met Asp Asn Ala His
            20                  25                  30

Gln Val Val Asn Ser Leu Asn Asn Glu Ala Gly Leu Pro Val Lys Leu
        35                  40                  45

Val Leu Lys Pro Leu Val Thr Thr Pro Asp Glu Ile Thr Ala Leu Cys
    50                  55                  60

Arg Glu Ala Asn Tyr Asp Thr Ala Cys Ile Gly Ile Met Thr Trp Leu
65                  70                  75                  80

His Thr Phe Ser Pro Ala Lys Met Trp Ile Gly Gly Leu Ser Ile Leu
                85                  90                  95

Asn Lys Pro Leu Leu Gln Phe His Thr Gln Phe Asn Ala Gln Ile Pro
            100                 105                 110

Trp Lys Thr Met Asp Ile Thr Ala Leu Cys Arg Glu Ala Asn Tyr Asp
        115                 120                 125

Thr Ala Cys Ile Gly Ile Met Thr Trp Leu His Thr Phe Ser Pro Ala
    130                 135                 140

Lys Met Trp Ile Gly Gly Leu Ser Ile Leu Asn Lys Pro Leu Leu Gln
145                 150                 155                 160

Phe His Thr Gln Phe Asn Ala Gln Ile Pro Trp Lys Thr Met Asp Val
                165                 170                 175

Ala Arg Phe Gly Asp Asn Met Arg Glu Val Ala Val Thr Glu Gly Asp
            180                 185                 190

Lys Val Ala Ala Gln Ile Gln Phe Gly Tyr Ser Val Asn Ala Tyr Gly
        195                 200                 205

Ile Gly Asp Leu Val Ala Val Val Asp Ala Val Ser Lys Gly Asp Ile
    210                 215                 220

Asp Thr Leu Val Glu Glu Tyr Glu Ala Thr Tyr Arg Phe Thr Asp Ala
225                 230                 235                 240

Val Lys Leu Asn Gly Asp Lys Arg Glu Asn Leu Leu Asp Ala Ala Arg
                245                 250                 255

Ile Glu Leu Gly Met Thr Arg Phe Leu Glu Gln Gly Gly Phe Lys Ala
            260                 265                 270

Phe Thr Thr Asn Phe Glu Asn Leu Tyr Gly Leu Lys Gln Leu Pro Gly
        275                 280                 285

Leu Ala Val Gln Arg Leu Met Gln Gln Gly Tyr Gly Phe Gly Gly Glu
    290                 295                 300

Gly Asp Trp Lys Thr Ala Ala Leu Leu Arg Ile Leu Lys Val Met Gly
305                 310                 315                 320

Thr Gly Leu Lys Gly Gly Thr Ser Phe Met Glu Asp Tyr Thr Tyr Asn
                325                 330                 335

Phe Gln Pro Gly Asn Asp Leu Val Val Gly Ser His Met Leu Glu Val
            340                 345                 350

Cys Pro Ser Ile Ala Lys Glu Glu Lys Pro Leu Leu Asp Val Gln His
        355                 360                 365

Leu Gly Ile Gly Gly Lys Ala Asp Pro Ala Arg Leu Ile Phe Ser Thr
    370                 375                 380
```

```
Pro Ala Gly Pro Ala Leu Asn Ala Ser Leu Ile Asp Met Gly Asn Arg
385                 390                 395                 400

Phe Arg Leu Leu Val Asn Val Val Asp Thr Val Glu Gln Pro His Pro
            405                 410                 415

Leu Pro Lys Leu Pro Val Ala Arg Ala Ile Trp Gln Ala Gln Pro Ser
            420                 425                 430

Leu Ala Thr Ala Ala Glu Ala Trp Ile Ile Ala Gly Gly Ala His His
            435                 440                 445

Thr Val Phe Ser Gln Ala Val Gly Val Asp Glu Leu Arg Leu Tyr Ala
            450                 455                 460

Glu Met His Gly Ile Glu Phe Leu Leu Ile Asp Asn Asp Thr Thr Leu
465                 470                 475                 480

Pro Ala Phe Lys Asn Glu Ile Arg Trp Asn Glu Val Tyr Tyr Gln Leu
            485                 490                 495

Asn Arg

<210> SEQ ID NO 6
<211> LENGTH: 497
<212> TYPE: PRT
<213> ORGANISM: B.stearotherm

<400> SEQUENCE: 6

Met Met Leu Ser Leu Arg Pro Tyr Glu Phe Trp Phe Val Thr Gly Ser
1               5                   10                  15

Gln His Leu Tyr Gly Glu Glu Ala Leu Lys Gln Val Glu Glu His Ser
            20                  25                  30

Met Met Ile Val Asn Glu Leu Asn Gln Asp Ser Val Phe Pro Phe Pro
            35                  40                  45

Leu Val Phe Lys Ser Val Val Thr Thr Pro Glu Glu Ile Arg Arg Val
        50                  55                  60

Cys Leu Glu Ala Asn Ala Ser Glu Gln Cys Ala Gly Val Ile Thr Trp
65                  70                  75                  80

Met His Thr Phe Ser Pro Ala Lys Met Trp Ile Gly Gly Leu Leu Glu
            85                  90                  95

Leu Arg Lys Pro Leu Leu His Leu His Thr Gln Phe Asn Arg Asp Ile
            100                 105                 110

Pro Trp Asp Ser Ile Asp Met Asp Phe Met Asn Leu Asn Gln Ser Ala
            115                 120                 125

His Gly Asp Arg Glu Tyr Gly Phe Ile Gly Ala Arg Met Gly Val Ala
            130                 135                 140

Arg Lys Val Val Gly His Trp Glu Asp Pro Glu Val Arg Glu Arg
145                 150                 155                 160

Leu Ala Lys Trp Met Arg Thr Ala Val Ala Phe Ala Glu Ser Arg Asn
            165                 170                 175

Leu Lys Val Ala Arg Phe Gly Asp Asn Met Arg Glu Val Ala Val Thr
            180                 185                 190

Glu Gly Asp Lys Val Gly Ala Gln Ile Gln Phe Gly Trp Ser Val Asn
            195                 200                 205

Gly Tyr Gly Ile Gly Asp Leu Val Gln Tyr Ile Arg Asp Val Ser Glu
            210                 215                 220

Gln Lys Val Asn Glu Leu Leu Asp Glu Tyr Glu Leu Tyr Asp Ile
225                 230                 235                 240

Val Pro Ala Gly Arg Gln Glu Gly Pro Val Arg Glu Ser Ile Arg Glu
            245                 250                 255
```

```
Gln Ala Arg Ile Glu Leu Gly Leu Lys Ala Phe Leu Gln Asp Gly Asn
            260                 265                 270

Phe Thr Ala Phe Thr Thr Thr Phe Glu Asp Leu His Gly Met Lys Gln
        275                 280                 285

Leu Pro Gly Leu Ala Val Gln Arg Leu Met Ala Glu Gly Tyr Gly Phe
290                 295                 300

Gly Gly Glu Gly Asp Trp Lys Thr Ala Ala Leu Val Arg Leu Met Lys
305                 310                 315                 320

Val Met Ala Asp Gly Lys Gly Thr Ser Phe Met Glu Asp Tyr Thr Tyr
                325                 330                 335

His Leu Glu Pro Gly Asn Glu Met Ile Leu Gly Ala His Met Leu Glu
            340                 345                 350

Val Cys Pro Thr Ile Ala Ala Thr Arg Pro Arg Ile Glu Val His Pro
        355                 360                 365

Leu Ser Ile Gly Gly Lys Glu Asp Pro Ala Arg Leu Val Phe Asp Gly
370                 375                 380

Gly Glu Gly Ala Ala Val Asn Ala Ser Leu Ile Asp Leu Gly His Arg
385                 390                 395                 400

Phe Arg Leu Ile Val Asn Glu Val Asp Ala Val Lys Pro Glu His Asp
                405                 410                 415

Met Pro Lys Leu Pro Val Ala Arg Ile Leu Trp Lys Pro Arg Pro Ser
            420                 425                 430

Leu Arg Asp Ser Ala Glu Ala Trp Ile Leu Ala Gly Gly Ala His His
        435                 440                 445

Thr Cys Phe Ser Phe Ala Val Thr Thr Glu Gln Leu Gln Asp Phe Ala
450                 455                 460

Glu Met Ala Gly Ile Glu Cys Val Val Ile Asn Glu His Thr Ser Val
465                 470                 475                 480

Ser Ser Phe Lys Asn Glu Leu Lys Trp Asn Glu Val Phe Trp Arg Gly
                485                 490                 495

Arg

<210> SEQ ID NO 7
<211> LENGTH: 497
<212> TYPE: PRT
<213> ORGANISM: B.halodurans

<400> SEQUENCE: 7

Met Leu Gln Thr Lys Pro Tyr Thr Phe Trp Phe Ile Thr Gly Ser Gln
1               5                   10                  15

His Leu Tyr Gly Glu Asp Ala Ile Glu Gln Val Arg Gln His Ser Gln
            20                  25                  30

Thr Met Val Glu Lys Leu Asn Lys Ile Gly Glu Leu Pro Tyr Thr Ile
        35                  40                  45

Glu Leu Lys Glu Val Leu Thr Thr Pro Asp Ala Ile Arg Lys Met Val
50                  55                  60

Ile Ala Ala Asn Ser Asp Asp Cys Ala Gly Met Ile Thr Trp Met
65                  70                  75                  80

His Thr Phe Ser Pro Ala Lys Met Trp Ile Asn Gly Leu Lys Gln Leu
                85                  90                  95

Lys Lys Pro Leu Leu His Leu His Thr Gln Phe Asn Arg Glu Ile Pro
            100                 105                 110

Tyr Asp Asp Ile Asp Met Asp Phe Met Asn Leu Asn Gln Ser Ala His
        115                 120                 125
```

-continued

```
Gly Asp Arg Glu Tyr Gly His Ile Gly Ala Arg Leu Asn Ile Ser Arg
    130                 135                 140

Lys Val Ile Val Gly His Trp Gln Asn Asn Asp Val Gln Glu Arg Leu
145                 150                 155                 160

Gly Ala Trp Met Arg Thr Ala Ala Phe Val Asp Gly His His Leu
                165                 170                 175

Lys Val Ala Arg Phe Gly Asp Asn Met Arg Glu Val Ala Val Thr Glu
                180                 185                 190

Gly Asp Lys Val Glu Ala Gln Ile Gln Phe Gly Trp Ser Ile Thr Ala
        195                 200                 205

Phe Gly Ile Gly Asp Leu Val Glu Lys Met Lys Ala Val Ser Glu Asp
    210                 215                 220

Glu Val Arg Arg Leu Phe Asp Glu Tyr Gln Glu Leu Tyr Arg Leu Ser
225                 230                 235                 240

Pro Ser Ile Leu Glu Gln Asp Glu Val Lys Ala Val Leu Glu Gln
                245                 250                 255

Ala Lys Met Glu Leu Ala Leu Lys Glu Phe Leu Glu Glu Gly Gly Tyr
        260                 265                 270

Thr Ala Phe Thr Thr Asn Phe Glu Asp Leu His Gly Met Lys Gln Leu
    275                 280                 285

Pro Gly Leu Ala Val Gln Arg Leu Met Ala Glu Gly Tyr Gly Phe Gly
    290                 295                 300

Gly Glu Gly Asp Trp Lys Thr Ala Ala Leu Leu Arg Met Met Lys Ile
305                 310                 315                 320

Ile Ala Asp Gly Lys Gly Thr Ser Phe Met Glu Asp Tyr Thr Tyr His
                325                 330                 335

Leu Ala Glu Gly Asn Glu Leu Val Leu Gly Ser His Met Leu Glu Ile
                340                 345                 350

Cys Pro Thr Ile Ala Ala Asn Gln Pro Glu Ile Gln Val His Pro Leu
            355                 360                 365

Gly Ile Gly Gly Lys Glu Asp Pro Ala Arg Leu Val Phe Asp Gly Ala
    370                 375                 380

Asp Gly Pro Ala Leu Asn Ala Ser Leu Ile Asp Leu Gly His Arg Phe
385                 390                 395                 400

Arg Leu Val Val Asn Glu Val Glu Ala Ile Lys Pro Glu Arg Asp Met
                405                 410                 415

Pro Lys Leu Pro Val Ala Lys Val Leu Trp Lys Cys Lys Pro Ser Leu
            420                 425                 430

Ser Glu Ala Thr Glu Ala Trp Ile His Ala Gly Gly Ala His His Thr
        435                 440                 445

Val Phe Ser Phe Glu Val Thr Pro Glu Gln Leu Tyr Asp Trp Ala Thr
    450                 455                 460

Leu Ala Asp Ile Glu Val Val Phe Ile Asn Asp Lys Thr Asp Val Leu
465                 470                 475                 480

Gln Phe Gln Gln Gln Leu Gln Trp Asn Glu Ala Phe Arg Arg Leu Phe
                485                 490                 495

Lys

<210> SEQ ID NO 8
<211> LENGTH: 498
<212> TYPE: PRT
<213> ORGANISM: B.subtilis

<400> SEQUENCE: 8
```

-continued

```
Met Leu Gln Thr Lys Asp Tyr Glu Phe Trp Phe Val Thr Gly Ser Gln
 1               5                  10                  15
His Leu Tyr Gly Glu Thr Leu Glu Leu Val Asp Gln His Ala Lys
             20                  25                  30
Ser Ile Cys Glu Gly Leu Ser Gly Ile Ser Ser Arg Tyr Lys Ile Thr
             35                  40                  45
His Lys Pro Val Val Thr Ser Pro Glu Thr Ile Arg Glu Leu Leu Arg
 50                  55                  60
Glu Ala Glu Tyr Ser Glu Thr Cys Ala Gly Ile Ile Thr Trp Met His
 65                  70                  75                  80
Thr Phe Ser Pro Ser Gln Lys Leu Trp Lys Arg Pro Phe Pro Pro
                 85                  90                  95
Tyr Gln Lys Pro Leu Met His Leu His Thr Gln Tyr Asn Arg Asp Ile
             100                 105                 110
Pro Trp Gly Thr Ile Asp Met Asp Phe Met Asn Ser Asn Gln Ser Ala
             115                 120                 125
His Gly Asp Arg Glu Tyr Gly Tyr Ile Asn Ser Arg Met Gly Leu Ser
 130                 135                 140
Arg Lys Val Ile Ala Gly Tyr Trp Asp Glu Glu Val Lys Lys Glu
 145                 150                 155                 160
Met Ser Gln Trp Met Asp Thr Ala Ala Ala Leu Asn Glu Ser Arg His
             165                 170                 175
Ile Lys Val Ala Arg Phe Gly Asp Asn Met Arg His Val Ala Val Thr
             180                 185                 190
Asp Gly Asp Lys Val Gly Ala His Ile Gln Phe Gly Trp Gln Val Asp
             195                 200                 205
Gly Tyr Gly Ile Gly Asp Leu Val Glu Val Met Asp Arg Ile Thr Asp
 210                 215                 220
Asp Glu Val Asp Thr Leu Tyr Ala Glu Tyr Asp Arg Leu Tyr Val Ile
 225                 230                 235                 240
Ser Glu Glu Thr Lys Arg Asp Glu Ala Lys Val Ala Ser Ile Lys Glu
             245                 250                 255
Gln Ala Lys Ile Glu Leu Gly Leu Thr Ala Phe Leu Glu Gln Gly Gly
             260                 265                 270
Tyr Thr Ala Phe Thr Thr Ser Phe Glu Val Leu His Gly Met Lys Gln
             275                 280                 285
Leu Pro Gly Leu Ala Val Gln Arg Leu Met Glu Lys Gly Tyr Gly Phe
             290                 295                 300
Ala Gly Glu Gly Asp Trp Lys Thr Ala Ala Leu Val Arg Met Met Lys
 305                 310                 315                 320
Ile Met Ala Lys Gly Lys Arg Thr Ser Phe Met Glu Asp Tyr Thr Tyr
             325                 330                 335
His Phe Glu Pro Gly Asn Glu Met Ile Leu Gly Ser His Met Leu Glu
             340                 345                 350
Val Cys Pro Thr Val Ala Leu Asp Gln Pro Lys Ile Glu Val His Ser
             355                 360                 365
Leu Ser Ile Gly Gly Lys Glu Asp Pro Ala Arg Leu Val Phe Asn Gly
             370                 375                 380
Ile Ser Gly Ser Ala Ile Gln Ala Ser Ile Val Asp Ile Gly Gly Arg
 385                 390                 395                 400
Phe Arg Leu Val Leu Asn Glu Val Asn Gly Gln Glu Ile Glu Lys Asp
                 405                 410                 415
Met Pro Asn Leu Pro Val Ala Arg Val Leu Trp Lys Pro Glu Pro Ser
```

-continued

```
                420                 425                 430
Leu Lys Thr Ala Ala Glu Ala Trp Ile Leu Ala Gly Gly Ala His His
        435                 440                 445
Thr Cys Leu Ser Tyr Glu Leu Thr Ala Glu Gln Met Leu Asp Trp Ala
    450                 455                 460
Glu Met Ala Gly Ile Glu Ser Val Leu Ile Ser Arg Asp Thr Thr Ile
465                 470                 475                 480
His Lys Leu Lys His Glu Leu Lys Trp Asn Glu Ala Leu Tyr Arg Leu
                485                 490                 495
Gln Lys
```

<210> SEQ ID NO 9
<211> LENGTH: 488
<212> TYPE: PRT
<213> ORGANISM: C.aceto7646

<400> SEQUENCE: 9

```
Met Leu Glu Asn Lys Lys Met Glu Phe Trp Phe Val Val Gly Ser Gln
1               5                   10                  15
His Leu Tyr Gly Glu Glu Ala Leu Lys Glu Val Arg Lys Asn Ser Glu
            20                  25                  30
Thr Ile Val Asp Glu Leu Asn Lys Ser Ala Asn Leu Pro Tyr Lys Ile
        35                  40                  45
Ile Phe Lys Asp Leu Ala Thr Ser Ala Asp Lys Ile Lys Glu Ile Met
    50                  55                  60
Lys Glu Val Asn Tyr Arg Asp Glu Val Ala Gly Val Ile Thr Trp Met
65                  70                  75                  80
His Thr Phe Ser Pro Ala Lys Met Trp Ile Ala Gly Thr Lys Ile Leu
                85                  90                  95
Gln Lys Pro Leu Leu His Phe Ala Thr Gln Tyr Asn Glu Asn Ile Pro
            100                 105                 110
Trp Lys Thr Ile Asp Met Asp Tyr Met Asn Leu His Gln Ser Ala His
        115                 120                 125
Gly Asp Arg Glu Tyr Gly Phe Ile Asn Ala Arg Leu Lys Lys His Asn
    130                 135                 140
Lys Val Val Val Gly Tyr Trp Lys Asp Lys Glu Val Gln Lys Gln Val
145                 150                 155                 160
Ser Asp Trp Met Lys Val Ala Ala Gly Tyr Ile Ala Ser Glu Ser Ile
                165                 170                 175
Lys Val Ala Arg Phe Gly Asp Asn Met Arg Asn Val Ala Val Thr Glu
            180                 185                 190
Gly Asp Lys Val Glu Ala Gln Ile Gln Phe Gly Trp Thr Val Asp Tyr
        195                 200                 205
Phe Gly Ile Gly Asp Leu Val Ala Glu Met Asp Lys Val Ser Gln Asp
    210                 215                 220
Glu Ile Asn Lys Thr Tyr Glu Glu Phe Lys Asp Leu Tyr Ile Leu Asp
225                 230                 235                 240
Pro Gly Glu Asn Asp Pro Ala Phe Tyr Glu Lys Gln Val Lys Glu Gln
                245                 250                 255
Ile Lys Ile Glu Ile Gly Leu Arg Arg Phe Leu Glu Lys Gly Asn Tyr
            260                 265                 270
Asn Ala Phe Thr Thr Asn Phe Glu Asp Leu Tyr Gly Met Lys Gln Leu
        275                 280                 285
Pro Gly Leu Ala Val Gln Arg Leu Asn Ala Glu Gly Tyr Gly Phe Ala
```

```
                290                 295                 300
Gly Glu Gly Asp Trp Lys Thr Ala Ala Leu Asp Arg Leu Leu Lys Val
305                 310                 315                 320

Met Thr Asn Asn Thr Ala Thr Gly Phe Met Glu Asp Tyr Thr Tyr Glu
                325                 330                 335

Leu Ser Arg Gly Asn Glu Lys Ala Leu Gly Ala His Met Leu Glu Val
                340                 345                 350

Asp Pro Thr Phe Ala Ser Asp Lys Pro Lys Val Ile Val Lys Pro Leu
                355                 360                 365

Gly Ile Gly Asp Lys Glu Asp Pro Ala Arg Leu Ile Phe Asn Gly Ser
370                 375                 380

Thr Gly Lys Gly Val Ala Val Ser Met Leu Asp Leu Gly Thr His Tyr
385                 390                 395                 400

Arg Leu Ile Ile Asn Gly Leu Thr Ala Val Lys Pro Asp Glu Asp Met
                405                 410                 415

Pro Asn Leu Pro Val Ala Lys Met Val Trp Lys Pro Glu Pro Asn Phe
                420                 425                 430

Ile Glu Gly Val Lys Ser Trp Ile Tyr Ala Gly Gly His His Thr
                435                 440                 445

Val Val Ser Leu Glu Leu Thr Val Glu Gln Val Tyr Asp Trp Ser Arg
450                 455                 460

Met Val Gly Leu Glu Ala Val Ile Ile Asp Lys Asp Thr Lys Leu Arg
465                 470                 475                 480

Asp Ile Ile Glu Lys Thr Thr Lys
                485

<210> SEQ ID NO 10
<211> LENGTH: 488
<212> TYPE: PRT
<213> ORGANISM: C.aceto7645

<400> SEQUENCE: 10

Met Leu Lys Asn Lys Leu Glu Phe Trp Phe Val Val Gly Ser Gln
1               5                   10                  15

Asn Leu Tyr Gly Glu Glu Ala Leu Asn Ala Val Lys Lys Asp Ser Lys
                20                  25                  30

Glu Ile Val Asp Ser Leu Asn Glu Ser Gly Lys Leu Pro Tyr Pro Ile
            35                  40                  45

Val Phe Lys Thr Leu Ala Thr Ser Ala Asp Glu Ile Lys Asn Ile Val
    50                  55                  60

Lys Glu Ile Asn Tyr Arg Asp Glu Val Ala Gly Val Ile Thr Trp Met
65                  70                  75                  80

His Thr Phe Ser Pro Ala Lys Met Trp Ile Ala Gly Thr Lys Leu Leu
                85                  90                  95

Gln Lys Pro Leu Leu His Leu Ala Thr Gln Phe Asn Glu Asn Ile Pro
            100                 105                 110

Trp Lys Thr Ile Asp Met Asp Tyr Met Asn Leu His Gln Ser Ala His
        115                 120                 125

Gly Asp Arg Glu Tyr Gly Phe Ile Asn Ala Arg Leu Asn Lys Asn Asn
    130                 135                 140

Lys Val Val Val Gly Tyr Trp Lys Asp Asn Val Gln Lys Glu Ile
145                 150                 155                 160

Ala Glu Trp Met Gln Val Ala Tyr Gly Tyr Val Ala Ser Glu Asn Ile
                165                 170                 175
```

-continued

```
Lys Val Ala Arg Phe Gly Asp Asn Met Arg Asn Val Ala Val Thr Glu
            180                 185                 190
Gly Asp Lys Val Glu Ala Gln Ile Gln Phe Gly Trp Thr Val Asp Tyr
        195                 200                 205
Phe Ala Ile Gly Asp Leu Val Ala Glu Met Asn Lys Val Ser Gln Lys
    210                 215                 220
Asp Ile Asp Ala Thr Tyr Glu Glu Phe Lys Asp Ile Tyr Ile Leu Asp
225                 230                 235                 240
Ile Gly Asp Asn Asp Pro Glu Phe Tyr Glu Asn His Val Lys Glu Gln
                245                 250                 255
Ile Lys Ile Glu Ile Gly Leu Arg Asn Phe Leu Glu Ala Gly Asn Tyr
            260                 265                 270
Thr Ala Phe Thr Thr Asn Phe Glu Asp Leu Tyr Gly Met Lys Gln Leu
        275                 280                 285
Pro Gly Leu Ala Val Gln Arg Leu Asn Ala Glu Gly Tyr Gly Phe Ala
    290                 295                 300
Gly Glu Gly Asp Trp Lys Thr Ala Ala Leu Asn Arg Leu Phe Lys Ile
305                 310                 315                 320
Met Thr Asp Asn Lys Lys Thr Gly Phe Met Glu Asp Tyr Thr Tyr Glu
                325                 330                 335
Leu Ser Ala Gly Asn Glu Arg Ile Leu Gly Ala His Met Leu Glu Val
            340                 345                 350
Asp Pro Thr Leu Ala Ala Ser Lys Pro Arg Val Val Lys Pro Leu
        355                 360                 365
Gly Ile Gly Asp Lys Glu Ala Pro Ala Arg Leu Ile Phe Asp Gly Val
    370                 375                 380
Val Gly Asp Gly Val Val Val Ser Met Leu Asp Leu Gly Thr His Tyr
385                 390                 395                 400
Arg Leu Leu Ile Asn Glu Val Lys Ala Val Lys Pro Thr Glu Asp Ala
                405                 410                 415
Pro Asn Leu Pro Val Ala Lys Leu Val Trp Gln Pro Gln Pro Asn Phe
            420                 425                 430
Lys Asp Ala Val Lys Ala Trp Ile Tyr Ala Gly Gly His His Thr
        435                 440                 445
Val Ala Thr Leu Glu Leu Thr Val Glu Gln Val Tyr Asp Trp Ser Arg
    450                 455                 460
Met Val Gly Leu Glu Thr Ile Val Ile Asp His Asn Thr Asn Leu Arg
465                 470                 475                 480
Asp Ile Ile Lys Glu Thr Ser Arg
                485
```

<210> SEQ ID NO 11
<211> LENGTH: 496
<212> TYPE: PRT
<213> ORGANISM: T.maritima

<400> SEQUENCE: 11

```
Met Ile Asp Leu Lys Gln Tyr Glu Phe Trp Phe Leu Val Gly Ser Gln
1               5                   10                  15
Tyr Leu Tyr Gly Leu Glu Thr Leu Lys Lys Val Glu Gln Gln Ala Ser
            20                  25                  30
Lys Ile Val Asp Ser Leu Asn Asp Asp Pro Ile Phe Pro Ser Lys Ile
        35                  40                  45
Val Leu Lys Pro Val Leu Lys Ser Ser Ser Glu Ile Thr Glu Ile Phe
    50                  55                  60
```

-continued

```
Glu Lys Ala Asn Ala Asp Pro Lys Cys Ala Gly Val Ile Val Trp Met
 65                  70                  75                  80

His Thr Phe Ser Pro Ser Lys Met Trp Ile Arg Gly Leu Ser Ile Asn
                 85                  90                  95

Lys Lys Pro Leu Leu His Leu His Thr Gln Tyr Asn Arg Glu Ile Pro
            100                 105                 110

Trp Asp Thr Ile Asp Met Asp Tyr Met Asn Leu Asn Gln Ser Ala His
        115                 120                 125

Gly Asp Arg Glu His Gly Phe Ile His Ala Arg Met Arg Leu Pro Arg
    130                 135                 140

Lys Val Val Gly His Trp Glu Glu Lys Glu Val Arg Glu Lys Ile
145                 150                 155                 160

Ala Lys Trp Met Arg Val Ala Cys Ala Ile Gln Asp Gly Arg Met Gly
                165                 170                 175

Gln Ile Val Arg Phe Gly Asp Asn Met Arg Glu Val Ala Ser Thr Glu
            180                 185                 190

Gly Asp Lys Val Glu Ala Gln Ile Lys Leu Gly Trp Ser Ile Asn Thr
        195                 200                 205

Trp Gly Val Gly Glu Leu Ala Glu Arg Val Lys Ala Val Pro Glu Arg
    210                 215                 220

Glu Val Glu Glu Leu Leu Lys Glu Tyr Arg Glu Lys Tyr Ile Met Pro
225                 230                 235                 240

Glu Asp Glu Tyr Ser Leu Lys Ala Ile Arg Glu Gln Ala Lys Ile Glu
                245                 250                 255

Ile Ala Leu Arg Glu Phe Leu Lys Glu Lys Asn Ala Val Gly Phe Thr
            260                 265                 270

Thr Thr Phe Glu Asp Leu His Asp Leu Pro Gln Leu Pro Gly Leu Ala
        275                 280                 285

Val Gln Arg Leu Met Glu Glu Gly Tyr Gly Phe Gly Ala Glu Gly Asp
    290                 295                 300

Trp Lys Ala Ala Gly Leu Val Arg Ala Ile Lys Val Met Gly Thr Ser
305                 310                 315                 320

Leu Pro Gly Gly Thr Ser Phe Met Glu Asp Tyr Thr Tyr His Leu Thr
                325                 330                 335

Pro Gly Asn Glu Leu Val Leu Gly Ala His Met Leu Glu Val Cys Pro
            340                 345                 350

Thr Ile Ala Lys Glu Lys Pro Arg Ile Glu Val His Pro Leu Ser Ile
        355                 360                 365

Gly Gly Lys Ala Asp Pro Ala Arg Leu Val Phe Asp Gly Gln Glu Gly
    370                 375                 380

Pro Ala Val Asn Ala Ser Ile Val Asp Met Gly Asn Arg Phe Arg Leu
385                 390                 395                 400

Val Val Asn Lys Val Leu Ser Val Pro Ile Glu Arg Lys Met Pro Lys
                405                 410                 415

Leu Pro Thr Ala Arg Val Leu Trp Lys Pro Leu Pro Asp Phe Lys Arg
            420                 425                 430

Ala Thr Thr Ala Trp Ile Leu Ala Gly Gly Ser His His Thr Ala Phe
        435                 440                 445

Ser Thr Ala Ile Asp Val Glu Tyr Leu Ile Asp Trp Ala Glu Ala Leu
    450                 455                 460

Glu Ile Glu Tyr Val Val Ile Asp Glu Asn Leu Asp Leu Glu Asp Phe
465                 470                 475                 480
```

```
Lys Lys Glu Leu Arg Trp Asn Glu Leu Tyr Trp Gly Leu Leu Lys Arg
                485                 490                 495
```

<210> SEQ ID NO 12
<211> LENGTH: 496
<212> TYPE: PRT
<213> ORGANISM: T.neapol

<400> SEQUENCE: 12

```
Met Ile Asp Leu Lys Gln Tyr Glu Phe Trp Phe Leu Val Gly Ser Gln
  1               5                  10                  15

Tyr Leu Tyr Gly Leu Glu Thr Leu Lys Lys Val Glu Gln Gln Ala Ser
             20                  25                  30

Arg Ile Val Glu Ala Leu Asn Asn Asp Pro Ile Phe Pro Ser Lys Ile
         35                  40                  45

Val Leu Lys Pro Val Leu Lys Asn Ser Ala Glu Ile Arg Glu Ile Phe
 50                  55                  60

Glu Lys Ala Asn Ala Glu Pro Lys Cys Ala Gly Val Ile Val Trp Met
 65                  70                  75                  80

His Thr Phe Ser Pro Ser Lys Met Trp Ile Arg Gly Leu Ser Ile Asn
                 85                  90                  95

Lys Lys Pro Leu Leu His Leu His Thr Gln Tyr Asn Arg Glu Ile Pro
            100                 105                 110

Trp Asp Thr Ile Asp Met Asp Tyr Met Asn Leu Asn Gln Ser Ala His
        115                 120                 125

Gly Asp Arg Glu His Gly Phe Ile His Ala Arg Met Arg Leu Pro Arg
130                 135                 140

Lys Val Val Gly His Trp Glu Asp Arg Glu Val Arg Glu Lys Ile
145                 150                 155                 160

Ala Lys Trp Met Arg Val Ala Cys Ala Ile Gln Asp Gly Arg Thr Gly
                165                 170                 175

Gln Ile Val Arg Phe Gly Asp Asn Met Arg Glu Val Ala Ser Thr Glu
            180                 185                 190

Asp Asp Lys Val Glu Ala Gln Ile Lys Leu Gly Trp Ser Ile Asn Thr
        195                 200                 205

Trp Gly Val Gly Glu Leu Ala Glu Gly Val Lys Ala Val Pro Glu Asn
210                 215                 220

Glu Val Glu Glu Leu Leu Lys Glu Tyr Lys Glu Arg Tyr Ile Met Pro
225                 230                 235                 240

Glu Asp Glu Tyr Ser Leu Lys Ala Ile Arg Glu Gln Ala Lys Met Glu
                245                 250                 255

Ile Ala Leu Arg Glu Phe Leu Lys Glu Lys Asn Ala Ile Ala Phe Thr
            260                 265                 270

Thr Thr Phe Glu Asp Leu His Asp Leu Pro Gln Leu Pro Gly Leu Ala
        275                 280                 285

Val Gln Arg Leu Met Glu Glu Gly Tyr Gly Phe Gly Ala Glu Gly Asp
    290                 295                 300

Trp Lys Ala Ala Gly Leu Val Arg Ala Leu Lys Val Met Gly Ala Gly
305                 310                 315                 320

Leu Pro Gly Gly Thr Ser Phe Met Glu Asp Tyr Thr Tyr His Leu Thr
                325                 330                 335

Pro Gly Asn Glu Leu Val Leu Gly Ala His Met Leu Glu Val Cys Pro
            340                 345                 350

Thr Ile Ala Lys Glu Lys Pro Arg Ile Glu Val His Pro Leu Ser Ile
        355                 360                 365
```

```
Gly Gly Lys Ala Asp Pro Ala Arg Leu Val Phe Asp Gly Gln Glu Gly
    370                 375                 380

Pro Ala Val Asn Ala Ser Ile Val Asp Met Gly Asn Arg Phe Arg Leu
385                 390                 395                 400

Val Val Asn Arg Val Leu Ser Val Pro Ile Glu Arg Lys Met Pro Lys
                405                 410                 415

Leu Pro Thr Ala Arg Val Leu Trp Lys Pro Leu Pro Asp Phe Lys Arg
                420                 425                 430

Ala Thr Thr Ala Trp Ile Leu Ala Gly Gly Ser His His Thr Ala Phe
                435                 440                 445

Ser Thr Ala Val Asp Val Glu Tyr Leu Ile Asp Trp Ala Glu Ala Leu
    450                 455                 460

Glu Ile Glu Tyr Leu Val Ile Asp Glu Asn Leu Asp Leu Glu Asn Phe
465                 470                 475                 480

Lys Lys Glu Leu Arg Trp Asn Glu Leu Tyr Trp Gly Leu Leu Lys Arg
                485                 490                 495

<210> SEQ ID NO 13
<211> LENGTH: 501
<212> TYPE: PRT
<213> ORGANISM: M.smegmatis

<400> SEQUENCE: 13

Met Ala Glu His Phe Thr Asp Glu Glu Ile Trp Phe Val Thr Gly Ser
1               5                   10                  15

Gln Ser Leu Tyr Gly Gln Glu Ile Leu Asp Gln Val Ala Glu Gln Ser
                20                  25                  30

Arg Ala Leu Ala Glu Arg Leu Asp Ala Ser Ala Asp Leu Pro Val Ala
            35                  40                  45

Val Arg Trp Lys Pro Val Val Thr Thr Ser Glu Ala Ile Leu Asp Val
    50                  55                  60

Leu Arg Asp Ala Ser Ser Ser Pro Gln Cys Val Gly Val Ile Thr Trp
65                  70                  75                  80

Met His Thr Phe Ser Pro Ala Lys Met Trp Ile Arg Gly Leu Ser Ala
                85                  90                  95

Leu Gln Lys Pro Met Leu His Leu His Thr Gln Phe Gly Val Glu Ile
                100                 105                 110

Pro Trp Asp Thr Ile Asp Met Asp Phe Met Asn Leu Asn Gln Ala Ala
            115                 120                 125

His Gly Asp Arg Glu Phe Gly Tyr Ile Gln Thr Arg Leu Ser Val Pro
    130                 135                 140

Arg Thr Thr Val Ala Gly His Val Gly Asp Pro Arg Thr Thr Ala Arg
145                 150                 155                 160

Ile Gly Ser Trp Met Arg Ala Ala Leu Gly Ala Ala Glu Leu Arg Ser
                165                 170                 175

Leu Arg Ile Ala Arg Phe Gly Asp Asn Met Arg Asp Val Ala Val Thr
                180                 185                 190

Glu Gly Asp Lys Val Glu Ala Glu Ser His Phe Gly Val Ser Val Asn
            195                 200                 205

Thr Tyr Ser Val Asn Asp Leu Ala Lys Ala Val Tyr Asp Val Ser Asp
    210                 215                 220

Pro Glu Ile Asp Lys Leu Val Gln Glu Tyr Glu Asp Thr Tyr Ala Val
225                 230                 235                 240

Ala Glu Glu Leu Arg Arg Gly Gly Glu Arg His Ala Ser Leu Arg Glu
```

```
                    245                 250                 255
Gly Ala Arg Ile Glu Leu Gly Leu Arg His Phe Leu Ala Asp Gly Phe
            260                 265                 270
Gly Ala Phe Thr Thr Asn Phe Glu Asp Leu Gly Asp Leu Arg Gln Leu
        275                 280                 285
Pro Gly Leu Ala Val Gln Arg Leu Met Ala Asp Gly Phe Gly Phe Gly
    290                 295                 300
Ala Glu Gly Asp Trp Lys Thr Ser Ala Met Val Arg Thr Val Lys Thr
305                 310                 315                 320
Met Gly Val Gly Leu Pro Gly Gly Thr Ser Phe Met Glu Asp Tyr Thr
            325                 330                 335
Tyr Asp Leu Thr Pro Gly Ser Glu Arg Ile Leu Gly Ala His Met Leu
        340                 345                 350
Glu Val Cys Pro Ser Ile Ala Gly Gln Thr Pro Ser Leu Glu Val His
    355                 360                 365
Pro Leu Gly Ile Gly Asn Arg Glu Asp Pro Val Arg Leu Arg Phe Thr
    370                 375                 380
Ala Ala Pro Gly Ser Gly Val Val Leu Gly Ile Cys Asp Met Gly Ser
385                 390                 395                 400
Arg Phe Arg Leu Val Ala Asn His Val Thr Val Glu Pro Ser Ala
            405                 410                 415
Pro Leu Pro Asn Leu Pro Val Ala Cys Ala Val Trp Glu Pro Glu Pro
            420                 425                 430
Ser Trp Ser Thr Ser Thr Glu Ala Trp Leu Met Ala Gly Gly Pro His
            435                 440                 445
His Thr Val Leu Thr Thr Ala Val Ser Pro Thr Thr Leu Asp Asp Phe
    450                 455                 460
Ala Thr Ile Thr Gly Thr Glu Leu Leu Gln Ile Asp Gln His Thr Thr
465                 470                 475                 480
Pro Arg Glu Phe Gln Arg Glu Met Arg Trp Asn Ala Val Tyr His His
            485                 490                 495
Ile Ala Ala Gly Leu
        500

<210> SEQ ID NO 14
<211> LENGTH: 407
<212> TYPE: PRT
<213> ORGANISM: T.mathranii

<400> SEQUENCE: 14

Ile Glu His Ile Val Lys Glu Phe Asn Glu Lys Asp Leu Asp Gly Ile
1               5                   10                  15
Met Ile Val Met Leu Thr Tyr Gly Pro Ala Thr Asn Ile Val Asn Ala
            20                  25                  30
Leu Arg Asn Asn Lys Leu Pro Ile Met Leu Ala Asn Ile Gln Pro Val
        35                  40                  45
Pro Thr Val Thr Glu Asp Trp Asp Met Gly Asp Leu Thr Tyr Asn Gln
    50                  55                  60
Gly Val His Gly Ala Gln Asp Thr Ala Asn Ala Ile Leu Arg Met Gly
65                  70                  75                  80
Ile Lys Cys Pro Ile Ile Thr Glu Glu Trp His Ser Glu Glu Phe Lys
            85                  90                  95
Lys Phe Val Gly Asp Trp Ala Lys Ala Val Gln Thr Ile Lys Ala Leu
            100                 105                 110
```

-continued

```
Arg Asn Met Lys Ile Ala Gln Phe Gly Arg Met His Gly Met Tyr Asp
        115                 120                 125
Ile Leu Gly Asp Asp Ala Ala Phe Thr Arg Lys Ile Gly Pro Gln Ile
        130                 135                 140
Asn Gln Glu Tyr Ile Gly Glu Val Tyr Arg Tyr Met Glu Thr Ala Thr
145                 150                 155                 160
Glu Glu Glu Ile Asn Ala Val Ile Glu Glu Asn Arg Lys Asn Phe Tyr
                165                 170                 175
Ile Asp Pro Asn Leu Ser Glu Glu Ser His Arg Tyr Ala Ala Arg Leu
            180                 185                 190
Gln Ile Gly Phe Lys Lys Phe Leu Ile Asn Lys Gly Tyr Asp Gly Phe
        195                 200                 205
Thr Ala His Phe Asp Val Phe Lys Gly Asp Gly Arg Phe Lys Gln Ile
        210                 215                 220
Pro Met Met Ala Ala Ser Asn Leu Met Ala Glu Gly Tyr Gly Tyr Ala
225                 230                 235                 240
Ala Glu Gly Asp Ala Val Thr Ala Ser Leu Val Ala Ala Gly His Val
                245                 250                 255
Leu Ile Gly Asp Ala His Phe Thr Glu Met Tyr Ala Met Asp Phe Lys
            260                 265                 270
Arg Asn Ser Ile Leu Met Ser His Met Gly Glu Gly Asn Trp Lys Ile
        275                 280                 285
Ala Arg Lys Asp Arg Pro Ile Lys Leu Ile Asp Arg Glu Leu Gly Ile
        290                 295                 300
Gly Lys Leu Asp Asn Pro Pro Thr Ile Val Phe Met Ala Gln Pro Gly
305                 310                 315                 320
Pro Ala Thr Leu Val Ser Leu Val Ser Leu Glu Gly Glu Arg Tyr Arg
                325                 330                 335
Leu Val Val Ser Lys Gly Glu Ile Leu Asp Thr Glu Glu Ala Lys Tyr
            340                 345                 350
Ile Glu Met Pro Tyr Phe His Phe Arg Pro Ser Thr Gly Val Lys Ala
        355                 360                 365
Cys Leu Asp Gly Trp Leu Thr Asn Gly Gly Thr His His Glu Cys Leu
        370                 375                 380
Asn Leu Gly Asp Asn Thr Arg Arg Trp Lys Ile Leu Cys Asn Leu Leu
385                 390                 395                 400
Asp Ile Glu Tyr Val Glu Val
                405
```

THERMOSTABLE ISOMERASE AND USE HEREOF, IN PARTICULAR FOR PRODUCING TAGATOSE

This application claims the benefit of U.S. Provisional Application 60/386,209 filed Jul. 16, 2001 which was converted to a provisional application from U.S. application Ser. No. 09/905,108, and claims the benefit of U.S. Provisional Application No. 60/305,155, filed Jul. 16, 2001, the content of both of which is incorporated herein by reference.

FIELD OF INVENTION

The present invention is within the field of industrial enzymes, in particular enzymes for synthesis of sugars such as D-tagatose.

TECHNICAL BACKGROUND AND PRIOR ART

D-tagatose is the keto-sugar corresponding to the aldosugar D-galactose. It has a sweetness value equivalent to sucrose but is poorly digested and has been found to be a useful, safe non-cariogenic low-calorie sweetener in food products, for which there is high demand.

D-tagatose can be synthesised chemically, e g. as described in U.S. Pat. No. 5,002,612

Enzymatic methods for production of D-tagatose have been described. Yamanaka and Wood (1966) list a number of lactic acid bacteria providing an L-arabinose isomerase enzyme capable of producing ketoses from L-arabinose, D-galactose or D-fucose.

U.S. Pat. No. 6,057,135 discloses a process for manufacturing D-tagatose, wherein a lactose permeate is hydrolysed to obtain a lactose hydrolysate comprising D-galactose and glucose. The hydrolysate is fermented to convert the glucose to ethanol which is subsequently removed and the remaining solution of D-galactose is subjected to enzymatic isomerisation with an L-arabinose isomerase to obtain D-tagatose. The L-arabinose isomerase preparations used are crude biomass extracts of *Lactobacillus pentosus, Bacillus amyloliquefaciens* or *Arthrobacter* spp WO 00/68397 describes the use of *E. coli* engineered for enhanced expression of *E. coli* L-arabinose isomerase for the production of tagatose.

WO 02/50282 describes the isolation of a thermostable L-arabinose isomerase capable of isomerising galactose. The amino acid sequence of this enzyme is closely related to previously known L-arabinose isomerase sequences, especially *Bacillus stearothermophilus*.

However, to date, enzymatic methods for production of tagatose have not been used commercially. There exists a high demand for new and improved low-calorie sweeteners, and consequently, improved methods for producing tagatose with higher efficiency and yield are highly needed in the industry.

A novel L-arabinose isomerase active enzyme has now been isolated and characterised. This enzyme exhibits a low sequence similarity when compared to all presently known L-arabinose isomerase sequences, including those disclosed in WO 00/68397 and WO 02/50282. The enzyme of the current invention has different substrate specificity as compared to prior art L-arabinose isomerases and it is a versatile alone isomerase capable of isomerising structurally related aldoses The enzyme is obtainable from a thermophilic microbial source and can thus be used at high operating temperatures.

SUMMARY OF INVENTION

In a first aspect of the invention, an isolated L-arabinose isomerase active enzyme is provided, which enzyme is derived from a *Thermoanaerobacter* species, or an isomerase active fragment hereof A second aspect of the invention is the provision of the nucleic acid coding for L-arabinose isomerase or an L-arabinose isomerase active fragment thereof, selected from the group consisting of: (i) a wild type nucleic acid isolated from a *Thermoanaerobacter* species and (ii) a nucleic acid sequence that is capable of hybridising with the sequence of (i) under stringent conditions.

In a further aspect is provided a nucleic acid construct comprising the above nucleic acid In a still further aspect of the invention there is provided a cell that is transformed with the above-mentioned nucleic acid or construct.

In a still further aspect, a method is provided for converting an aldose into a ketose, comprising contacting the aldose with the isomerase of the invention and keeping the reaction under conditions where at least 1 wt % of the aldose is converted into the corresponding ketose.

The invention provides in yet a further aspect a method of producing L-arabinose isomerase, comprising transforming a cell with the nucleic acid of the invention and operably linking thereto appropriate expression signals directing the expression of the isomerase and, optionally, sequences directing the secretion of the isomerase, propagating said transformed cell and harvesting the progeny cells containing the isomerase or, if it is secreted into the medium, the excreted isomerase In a still further aspect, the invention provides a composition comprising the isomerase of the invention in an immobilised form.

Another aspect of the invention provides a method of producing D-tagatose comprising hydrolyzing lactose by contacting the lactose with a lactase-active enzyme to yield glucose and D-galactose, and converting at least a portion of the obtained D-galactose to D-tagatose by contacting the D-galactose with an L-arabinose isomerase-active enzyme, wherein said lactase-active enzyme and said L-arabinose isomerase-active enzyme are contained in the same reactor unit under essentially the same reaction conditions.

DETAILED DESCRIPTION

As stated above, the invention described herein provides a novel L-arabinose isomerase active enzyme or an isomerase active fragment thereof, which is derived from a *Thermoanaerobacter* species.

L-arabinose isomerase (EC 5.3.1.4) also referred to as L-arabinose ketol-isomerase, falls within the general class of intramolecular oxidoreductases and more specifically, the group of aldose isomerases, which are capable of interconverting aldoses to their corresponding ketoses. The L-arabinose isomerase is classified and named according to its ability to convert the aldose L-arabinose to its corresponding ketose, L-ribulose The term "isolated" as used herein means that the material is removed from its original environment (e g. the natural environment where the material is naturally occurring). For example, a polynucleotide or polypeptide while present in a living organism is not isolated, but the same polynucleotide or polypeptide, which is separated from some or all of the coexisting materials in the natural system, is isolated. Such polynucleotides could be part of a vector and/or such polynucleotides or polypeptides could be part of a composition, and still be isolated in that the vector or composition is not part of the natural environment The *Thermoanaerobacter* genus includes a range of species such as *T. acetoethylicus, T brockii, T. cellulolyticus, T. ethanolicus, T. finnii, T. italicus, T. kivui, T. mathranii, T. siderophilus, T. subterraneus, T. sulfurophilus, T. thermohydrosulfuricus* and *T. wiegelii*. In a presently preferred embodiment, the isomerase enzyme or active fragment thereof is obtained from the species *T. mathranii*, of which a useful strain (DSMZ 11426) is obtainable from Deutsche Sammlung von Mikroorganismen und Zellkulturen GmbH (DSMZ).

The isomerase of the invention preferably has at least one of the following characteristics: (i) an optimum activity at a temperature in the range of 40 to 95° C., preferably in the range of 60 to 80° C., such as in the range of about 60 to 70° C., including about 65° C., (ii) optimum activity at a pH in the range of 6 to 9, preferably in the range of 7 to 9, such as in the range of about pH 7 to 8; and (iii) is capable of isomerising at least one aldopentose or at least one aldohexose. Aldopentoses are five-carbon aldoses which include e.g. arabinose, ribose, xylose and lyxose, whereas aldohexoses are six-carbon sugars, including allose, altrose, glucose, mannose, gulose, idose, galactose and talose. More preferably, the isomerase has at least two of these characteristics and most preferably all three of these characteristics. Reaction temperatures of 60° C. and higher such as at least 65, 70, 75 or 80° C. are preferred, as the contamination risk from growth of other microorganisms is minimised at such elevated temperatures. Furthermore, high temperatures allow the use of higher substrate concentrations due to the increased substrate solubility. The preferred isomerase from *T mathranii* has an excellent temperature profile in this respect, with maximum activity at around 65° C., and about or more than 70% of the maximum activity is retained in the temperature range of about 60–75° C.

Yet further advantages of performing the isomerization at a high temperature are.

(i) that the equilibrium between aldose and ketose is shifted towards ketose at higher temperatures. (For L-arabinose isomerase fra *Lactobacillus plantarum* it has been reported that the amount of ketose at 10° C., 25° C. og 53° C. is 10%, 14% and 16% respectively (Heath, E. C., Horecker, B. L., Smyrniotis, P. Z. and Takagi, Y. (1958) *J. Biol. Chem.* 231: 1031–1037).

(ii) the substrate specificity towards D-galactose is higher relative to L-arabinose at higher temperatures U.S. Pat. No. 6,057,135 8 (Krafts Foods, Inc., Example 5) discloses L-arabinose isomerase fra *Lactobacillus pentosus* having relative specificity for L-ara.D-gal of 300:1 at 35° C. and 85:1 at 60° C.

Compared to the known L-arabinose isomerases, the isomerases of the current invention appear to be relatively versatile aldose isomerases which are able to isomerise many structurally related aldoses Preferably, the isomerases of the invention are capable of isomerising at least all of L-arabinose, D-galactose and D-fucose. These three aldoses have the same chiral configuration from C-1 to C-4. In particular, for the production of D-tagatose, isomerases being capable of efficient isomerisation of D-galactose are highly desirable.

The isomerase of the invention is derived from a thermophilic source, which endows it with both a high activity at elevated temperatures, such as within the temperature ranges mentioned above, for extended periods of time, and good stability against thermal denaturation. It is contemplated that related L-arabinose isomerases from other thermophilic sources will have similar suitable characteristics.

The activity of the enzyme towards L-arabinose and D-galactose may conveniently be assayed as described in Example 2 or by any other applicable methods known in the art The specificity can be further defined by comparative activity measurements for other aldose substrates.

In one embodiment of the invention, the isomerase has the amino acid sequence of SEQ ID NO:2 herein. Variants and derivatives thereof are also encompassed by the invention including such variants and derivatives that have isomerase activity and showing at least 70% sequence identity to this sequence, including at least 75% or at least 80% sequence identity, such as at least 90% sequence identity, and preferably at least 95% or 97% sequence identity. Useful variants and derivatives may e g. be obtained by isolation from microbial species such as those mentioned above and/or by genetic modification of organisms naturally producing isomerases such as by site-directed mutagenesis, or e g. by insertion of a sequence coding for an affinity tag such as a His-tag.

Alternative methods for providing variants of the invention include gene-shuffling methods which have become available, e.g., as described in Merz et al *Biochemistry* (2000) 39: 880–889, J. Minshull *Curr. Op. Chem Biol.* (1999) 3:284–290, WO 95/22625 (Affymax Technologies N.V.), U.S. Pat. No. 6,291,165 (Novo Nordisk A/S), U.S. Pat. No. 6,132,970 and U.S. Pat. No. 6,372,497 (Maxygen, Inc.). Briefly, gene shuffling techniques involves providing a plurality of related genes or nucleic acid sequences (e.g., sequences coding for different L-arabinose isomerases of the present invention) that are randomly fragmented and then reassembled by a reaction in which homologous fragments (or conserved regions of heterologous fragments) act as primers for each other, The thus obtained variants can be screened and selected based on various criteria. The shuffling techniques are particularly beneficial in this respect, as they allow the combination of different desired properties from different related proteins. With respect to the isomerases of the present invention, desired properties that can be combined by shuffling techniques and screened for with applicable methods of the art include substrate specificity, temperature stability, optimum temperature, long-term stability, expression efficiency in a selected host organism, etc.

"Sequence identity" as used herein is calculated based on a reference sequence, (which in this instance is the sequence of SEQ ID NO 2). Algorithms for sequence analysis are known in the art, such as e.g. BLAST, described in Altschul et al., *J. Mol. Biol* (1990) 215:403–10. Generally, the default settings with respect to e.g. "scoring matrix" and "gap penalty" will be used for alignment As seen in FIG. 2 and discussed in Example 1, the presently preferred isomerase of the invention derived from *Thermoanaerobacter mathranii*, has low sequence identity (24–30%) with known L-arabinose isomerases, which all show significantly higher identity to each other. This may explain differences in the kinetic characteristics and specificity from prior art L-arabinose isomerases.

Preferred isomerases of the present invention have a molecular weight in the range of about 50–60 kDa and more preferably in the range of about 52–55 kDa, including about 53 kDa. However, the isomerase active fragments of the invention may have a significantly lower molecular weight as they may contain only a small portion of a wild type isomerase sequence necessary for correct folding of the polypeptide and retention of activity The highly preferred L-arabinose isomerase derived from *T. mathranii* has a full length molecular weight of 53 kDa calculated on the basis of the sequence of Table 1.2 herein (SEQ ID NO:2). Many of the preferred isomerases of the invention, including the full length isomerase derived from *T. mathranii*, have a tetramer quaternary structure in the native, active state of the protein The term "isomerase active fragment" refers generally to any fragment of an isomerase of the present invention, which fragment is sufficiently large to substantially retain the activity of the isomerase from which it is obtained. While the active site of arabinose isomerase has not been characterized in detail, a comparison with the related L-fucose isomerase from *E. coli* (Seemann, J. E. and Schulz, G. E. (1997) *J. Mol. Biol.* 273:256–268) is suggestive of active site residues. Catalytically active residues in the fucose isomerase are Glu337 and Asp 361. An alignment of known L-arabinose isomerases with the L-fucose isomerase shows that the glutamic acid residue is conserved among all the known L-arabinose isomerases (Glu300 in the *T. mathranii* L-arabinose isomerase). The aspartic acid is conserved in all the L-arabinose isomerase sequences except the *T. mathranii* sequence, which has a methionine in the corresponding position (Met324) (see FIG. 4). Residues that may act as proton donors are Asp318, Glu323 and Asp 328. Consequently, it is postulated that the key active site residues are located in the region between amino acid residues 290–340. Thus, useful isomerase active fragments of the present invention may include a sequence fragment comprising residues within the region of 150–462, or e.g. 200–460, such as within the region of 200–400, or 250–400, including the region of 270–350, or the region of 290–340 Such fragment may be folded in a tetrameric quaternary structure, or possibly retain its activity but having a different quaternary structure, e.g. a monomeric structure. Further, an isomerase fragment of the invention may in certain embodiments be combined with other suitable polypeptide sequences that do not hinder the isomerase activity but may improve features such as, eg. overexpression, solubility and/or stability, to obtain a chimeric protein comprising an isomerase active fragment sequence.

In useful embodiments, the isomerase of the invention has a $K_m$ value for D-galactose in the range of about 50 to 350 mM, including the range of 100 to 200 mM. Certain preferred isomerases of the invention have similar $K_m$ also for L-arabinose. A standard definition of $K_m$ can be found in Stryer, L. *Biochemistry* 3rd ed., Freeman, N.Y., 1988. It follows that the substrate affinity of such preferred isomerases for D-galactose vs. L-arabinose is comparatively high in comparison to prior art isomerases, as shown in Table 2.1 herein.

Preferably the isomerase according to the invention has a D-galactose activity which is about 10 to 50% of its L-arabinose activity, such as in the range of 15–30%, including the range of about 20–25%.

Preferred isomerases of the present invention show a high conversion efficiency for the conversion of D-galactose to D-tagatose, even at high substrate concentrations. Preferably, the isomerases of the invention are capable of converting at least 20 wt % of D-galactose which is at a concentration of about 30 wt % or higher in the reaction medium, in a 24 h period.

The invention provides in a further aspect an L-arabinose isomerase capable of isomerising D-galactose to D-tagatose, which isomerase has at least 60% sequence identity to the sequence of SEQ ID NO:2 herein or higher, such as at least 70% or at least 80% sequence identity or at least 90% sequence identity SEQ ID NO:2, and an isomerase active fragment thereof. In particular embodiments the isomerase may have even higher sequence identity to SEQ ID NO:2, such as at least 95% or at least 97% sequence identity.

Preferably the isomerase is derived from a thermophilic organism, such as a bacterium which is taxonomically related to the genus *Thermoanaerobacter*.

In another aspect, the invention provides a nucleic acid coding for L-arabinose isomerase or an L-arabinose isomerase active fragment hereof, selected from the group consisting of: (i) a wild type nucleic acid isolated from a *Thermoanaerobacter* species and (ii) a nucleic acid sequence that is capable of hybridising with the aforementioned sequence under stringent conditions.

The term "nucleic acid" as used herein, includes DNA (e.g. genomic DNA or cDNA), and RNA, with naturally occurring nucleotides as well as containing one or more modified bases. Thus, DNAs or RNAs with backbones modified for stability or for other reasons are nucleic acids as defined herein. Moreover, DNAs or RNAs comprising unusual bases, such as inosine, or modified bases, such as tritylated bases, to name just two examples, are nucleic acids as the term is used herein.

The term "stringent conditions" in this context refers to general conditions of high stringency The term "stringency" is well known in the art and is used in reference to the conditions (temperature, ionic strength and the presence of other compounds such as organic solvents) under which nucleic acid hybridisations are conducted. With "high stringency" conditions, nucleic acid base pairing will occur only between nucleic acid fragments that have a high frequency of complementary base sequences, as compared to conditions of "weak" or "low" stringency.

As an example, high stringency hybridisation conditions include (1) employ low ionic strength and high temperature for washing, such as 0.015 M NaCl/0.0015 M sodium citrate, pH 7.0 (0.1×SSC) with 0.1% sodium dodecyl sulfate (SDS) at 50° C.; (2) employ during hybridisation 50% (vol/vol) formamide with 5× Denhardt's solution (0.1% (wt/vol) highly purified bovine serum albumin/0.1% (wt/vol) Ficoll/0.1% (wt/vol) polyvinylpyrrolidone), 50 mM sodium phosphate buffer at pH 6.5 and 5×SSC at 42° C.; or (3) employ hybridisation with 50% formamide, 5×SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C. with washes at 42° C. in 0.2×SSC and 0.1% SDS.

In a preferred embodiment, the nucleic acid coding for said isomerase or fragment thereof is the wild type nucleic acid isolated from *Thermoanaerobacter mathranii*, or a sequence that is capable of hybridising with such sequence under stringent conditions.

In a useful embodiment, the nucleic acid of the invention codes for the amino acid of SEQ ID NO:2 herein, or an isomerase-active fragment thereof. However, also encompassed by the invention are nucleic acids coding for isomerase-active polypeptides with high sequence identity to SEQ ID NO:2 or an isomerase-active part thereof, such as with a sequence identity as defined above of at least 75%, and preferably 90% or higher, such as 95% or 97%.

A particular embodiment of the invention provides the nucleic acid having the sequence of SEQ ID:1, which is shown in Table 1.1, or a fragment thereof coding for an isomerase active fragment.

In yet a highly useful aspect, the invention provides a nucleic acid construct comprising the nucleic acid of the invention. A "nucleic acid construct" as used herein includes a plasmid, virus, retrovirus, bacteriophage, transposon; cosmid, artificial chromosome (bacterial or yeast), that is able to replicate in a host cell and which typically has one or more restriction endonuclease recognition sites at which the sequence may be cut in a predetermined fashion. The construct can also contain a marker suitable for use in the identification of transformed cells, e.g., tetracycline resistance or ampicillin resistance.

Also encompassed by the invention is a cell that is transformed with either the above described nucleic acid or construct. A "cell" as used herein, refers to any prokaryotic or eukaryotic cell which is used as a recipient of the recombinant polynucleotides and constructs provided herein. In preferred embodiments, the transformed cell of the invention is a bacterial cell, a yeast cell or a cell of a filamentous fungus. A host cell such as *E coli* may be employed in this regard, however, preferred host cells are those that are readily compatible with food production. Examples of suitable bacterial host cells are *Bacillus* spp.e.g. *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium,* and *Bacillus thuringiensis,* or *Streptomyces lividans* or *Streptomyces murinus,* or *Lactococcus* spp., *Lactobacillus* spp. and *Zymomomas* spp. Useful yeast host cells include cells of *Saccharomyces* spp (in particular *S. cerevisiae*), *Schizosaccharomyces* spp., and *Pichia* spp. and useful cells of filamentous fungi include those of *Aspergillus* spp. such as *A. niger, A nidulans* and *A. oryzae; Mucor* spp, e.g. *Mucor circinelloides*; and *Neurospora* spp., e.g. *Neurospora crassa*.

Methods of transforming cells such as those mentioned above with a nucleic acid or construct as those mentioned above are well known in the art. The construct or nucleic acid may be introduced into the host cells using any suitable method (e.g. electroporation, transfection using calcium chloride, rubidium chloride, calcium phosphate, DEAE-dextran, or other substances, microprojectile bombardment, lipofection, infection, transduction)

Yet a further aspect of the invention provides a method of converting an aldose into a ketose, the method comprising contacting the aldose with the L-arabinose isomerase of the invention and keeping the reaction under conditions where at least 1 wt % of the aldose is converted. Preferably, conditions are selected such that at least 10 wt % of the substrate aldose is converted to its corresponding ketose, and more preferably at least about 20%, including about 25%, and even more preferably at least about 30% or more of the aldose is converted to ketose.

The aldose may be any of those mentioned above and is preferably selected from the group consisting of L-arabinose, D-galactose and D-fucose. A highly useful embodiment of the invention uses D-galactose as the aldose, in which case the reaction product ketose is D-tagatose. D-galactose may be readily obtained by hydrolysing lactose, obtained on a commercial scale from cheese whey and/or milk.

In a preferred embodiment of method, the reaction takes place at a temperature of at least 60° C., such as in the range of 60–100° C., including about 60–80° C., and preferably in a range of about 60–70° C.

Manganese ions ($Mn^{+2}$) may be required to sustain the activity of at least some of the isomerases of the invention. Consequently, in useful embodiments of the invention $Mn^{+2}$ is present in the reaction mixture at a concentration in the range of about 1–20 mM, including about 1–10 mM such as in the range of about 2–5 mM. However, some of the preferred isomerases still retain substantially all of their activity if $Fe^{+2}$ ions are present at a concentration such as those just mentioned, or higher.

High substrate concentrations are generally advantageous in the industrial production of D-tagatose using the method of the invention, such as 5 wt % or higher, preferably 10 wt % or higher and more preferably 30 wt % or higher, such as in the range of 30–60 wt %. As discussed above, the isomerases of the present invention have good conversion efficiency of D-galactose at such substrate concentrations and the high operating temperatures benefit high substrate solubility.

The L-arabinose isomerase may suitably be provided as an isolated enzyme preparation. Methods of isolating the isomerase from its source can be readily selected and adjusted by the skilled person to obtain the isolated enzyme of desired purity. Such methods may comprise one or more steps of chromatographic purification by ion exchange, affinity, and gel permeation chromatography, and/or may include steps of sonification, centrifugation and/or ultrafiltration.

Preferably, the isomerase is purified to an extent where it is essentially without any other proteins. In this context "essentially without any other proteins" refers to a high degree of purity, wherein other proteins comprise less than 10 wt % of the purified isomerase preparation, preferably less than 5 wt % and more preferably less than 3 wt %, such as substantially 0 wt % of the preparation.

The enzyme of the invention may advantageously be used as a free, non-immobilised enzyme, but in other useful embodiments, the isolated isomerase enzyme preparation is immobilised. In the present context, the term 'immobilised' refers generally to the binding (covalent or non-covalent) of the enzyme to a solid matrix such as beads, fibres or a membrane or imbedding the enzyme within a porous matrix, such that the enzyme-matrix contact is withheld during normal reaction conditions. Methods of immobilising an enzyme are well known in the art and include as an example cross-linking with glutaraldehyde as it is demonstrated in Example 3. Other applicable methods are e.g. coupling of the enzyme to matrix hydroxyl groups that are activated by e.g. a carbodiimide, carbonyl diimidazole, N,N'-disuccinimidyl carbonate (DSC), or cyanogen bromide; and coupling by epoxidation by e.g. 1,4-butanediol diglycidyl ether.

As shown in Example 3.3 herein, immobilised isomerase of the invention is shown to have excellent long-term stability during repeated reaction cycles at relatively high operating temperatures (65° C.), and thus is highly suitable for industrial applications.

It has been found that a two-step process of (i) hydrolysing lactose to glucose and galactose and (ii) isomerising the obtained galactose to tagatose can be performed in a single reactor; that is, a suitable lactase-active enzyme and an L-arabinose isomerase of the present invention can be used simultaneously in one reaction unit which is fed with lactose to obtain tagatose. An embodiment of this is demonstrated and described in detail in Example 4. Surprisingly, the obtained glucose does not hinder the activity of the isomerase, and the glucose may be separated from the tagatose as well as any non-isomerized galactose with suitable separation means, such as chromatography Such a two-step one-reactor process is conveniently setup by use of immobilized lactase and immobilized L-arabinose isomerase, where both enzymes may be immobilized e.g. as described herein. Preferably, the lactase should retain its activity at a high temperature, e.g. in the range of 60–100° C., including the range of 60–80° C. and 60–70° C., such that the high-temperature regime of the isomerase can be utilized, as described herein. One preferred lactase enzyme in this regard is β-glycosidase which is readily available from various sources, e.g. derived from thermophilic bacteria and expressed in a suitable host such as *E. coli*, but more preferably in a more compatible and better approved food production host cell, such as are mentioned herein.

Based on the above findings, the invention thus provides in a further aspect, a method of producing D-tagatose comprising hydrolyzing lactose by contacting the lactose with a lactase-active enzyme (in most cases being a β-galactosidase) to yield glucose and D-galactose, and converting at least a portion of the obtained D-galactose to D-tagatose by contacting the galactose with an L-arabinose isomerase-active enzyme, wherein said lactase-active enzyme and said L-arabinose isomerase-active enzyme are contained in the same reactor unit under essentially the same reaction conditions. In particularly useful embodiments the reaction conditions include a temperature in the range of about 50 to about 100° C., preferably of about 55 to about 100° C., and more preferably in a range of about 60 to about 100° C., such as in the range of about 60 to about 80° C., including the range of about 65 to about 80° C., such as in the range of about 65 to about 75° C., including about 65° C., about 70° C., and about 75° C. In addition, the reaction conditions will typically include such conditions as described above, such as a pH in the range of 6 to 9, preferably in the range of 7 to 9, such as in the range of about pH 7 to 8

D-tagatose produced by the methods of the present invention finds use in a variety of food, functional food, and pharmaceutical applications. It is a low-calorie full bulk sweetener which can advantageously replace, fully or partially, sugar and/or non-sugar sweeteners in conventional sweet products such as candies, chocolate, cereals, sweet dairy products (ice cream, yoghurt, milk-based drinks), baked goods, and soft drinks. The D-tagatose can further be used in diet health bars, sugarless chewing gum and as a sweetening filler in medicinal products such as pills, lozenges and liquid mixtures. D-tagatose is non-cariogenic and has probiotic properties that promote healthy digestion. The compound is safe for use by people with diabetes.

In a still further aspect of the invention there is provided a method of producing L-arabinose isomerase, comprising transforming a cell such as of those described above with a nucleic acid of the invention and operably linking thereto appropriate expression signals directing the expression of the isomerase and, optionally, sequences directing the secretion of the isomerase, propagating the thus transformed cell and harvesting the progeny cells containing the isomerase or, if it is secreted into the medium, the excreted isomerase. The term "transforming" refers to changing in a heritable manner the characteristics of a host cell in response to the introduced exogenous DNA, which may or may not be integrated (covalently linked) to chromosomal DNA making up the genome of the cell. In prokaryotes and yeast, for example, the exogenous DNA may be maintained on an episomal element such as a plasmid. With respect to eukaryotic cells, a stably transformed cell is one in which the exogenous DNA has been integrated into a chromosome so that it is inherited by daughter cells through chromosome replication. This stability is demonstrated by the ability of the eukaryotic cell to establish cell lines or clones comprised of a population of daughter cells containing the exogenous DNA.

In useful embodiments, the method of the invention comprises the further step of purifying the L-arabinose isomerase from the progeny cells or the medium to obtain an L-arabinose isomerase preparation, e.g. with purification methods such as those described above.

In one embodiment, the method comprises the further step of drying the isomerase preparation to a moisture content of at the most 10 wt %. Such a preparation can be in a powder or granular form, which may suitably be re-dissolved in a medium for using the isomerase as described herein.

In a still further aspect, the invention provides a composition comprising the L-arabinose isomerase described herein in an immobilised form e.g. an immobilised form such as is described herein.

Figure 3:
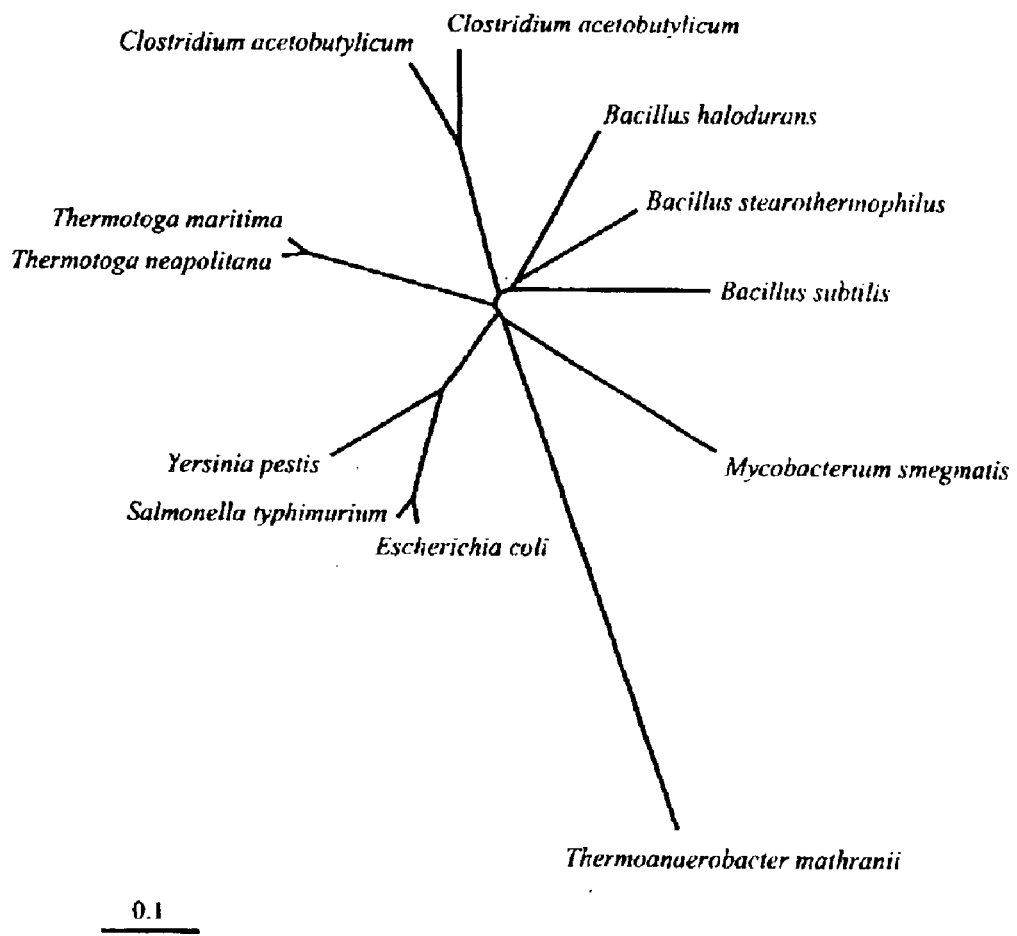
Figure 4A:
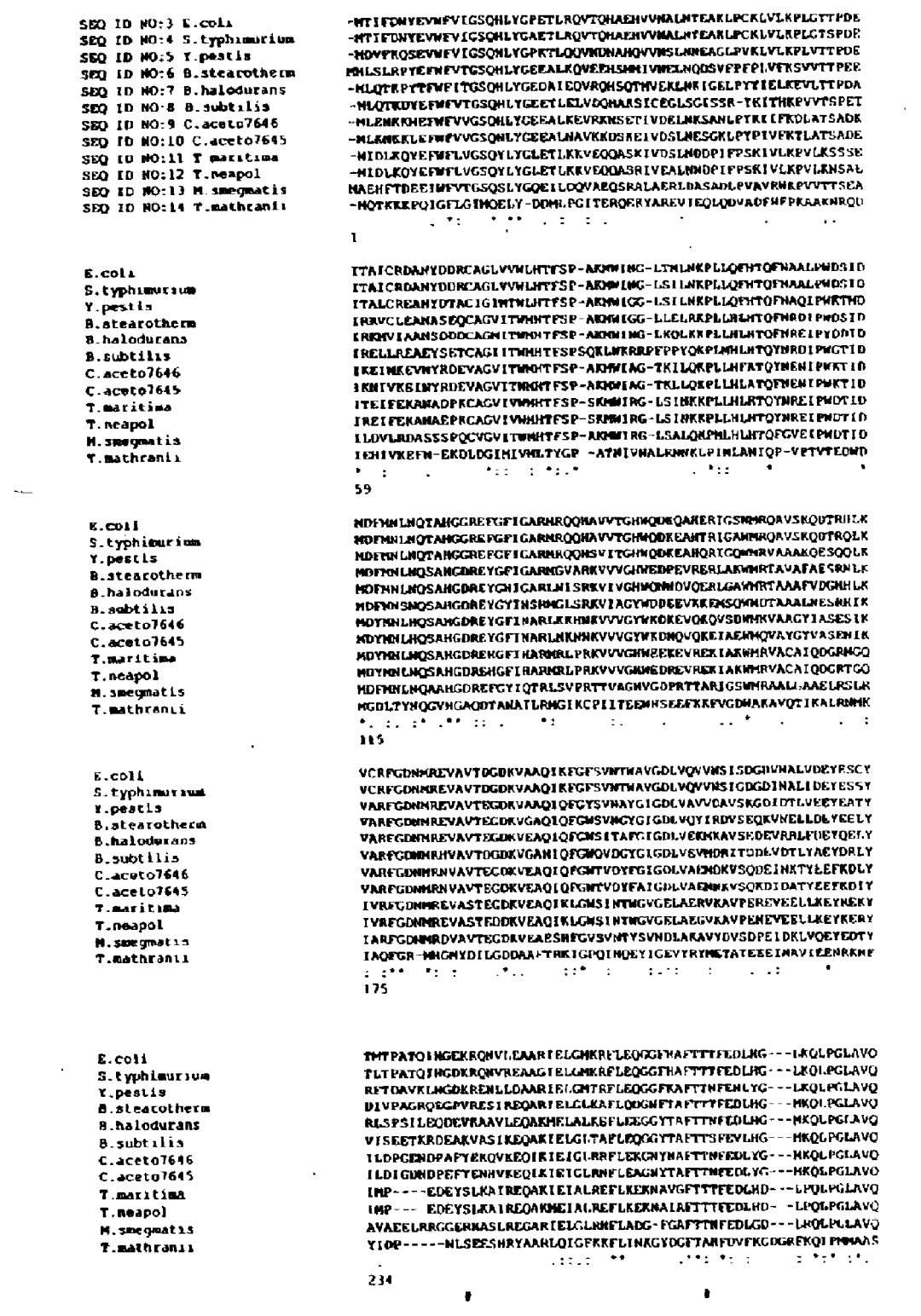
Figure 5:
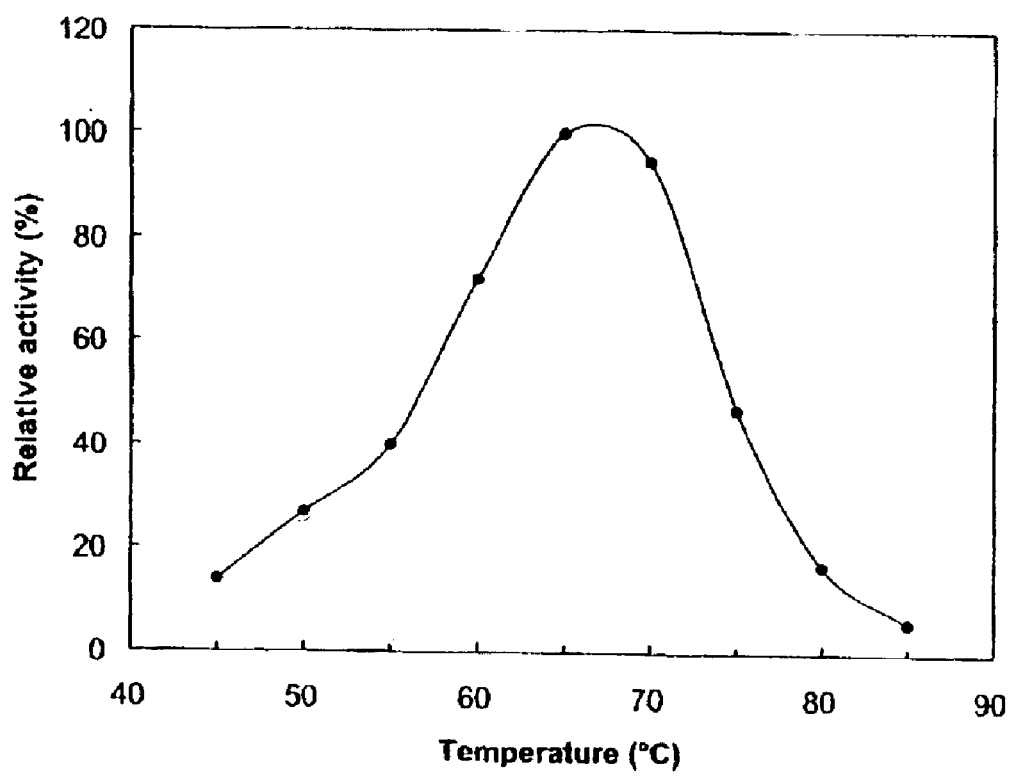
Figure 6:
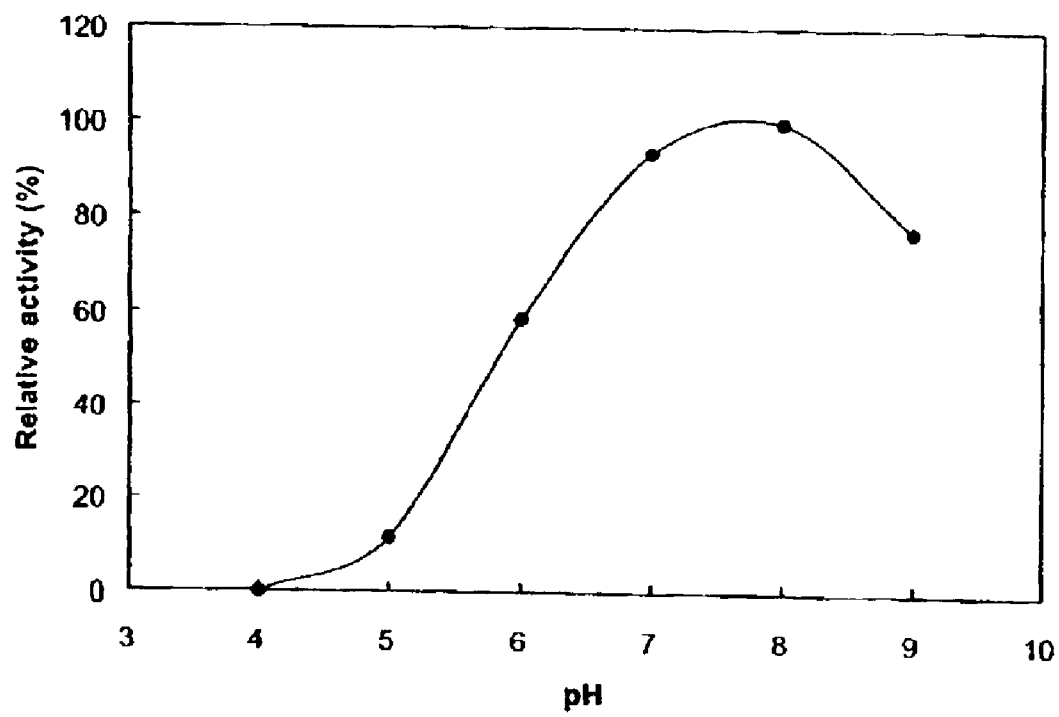
Figure 7:
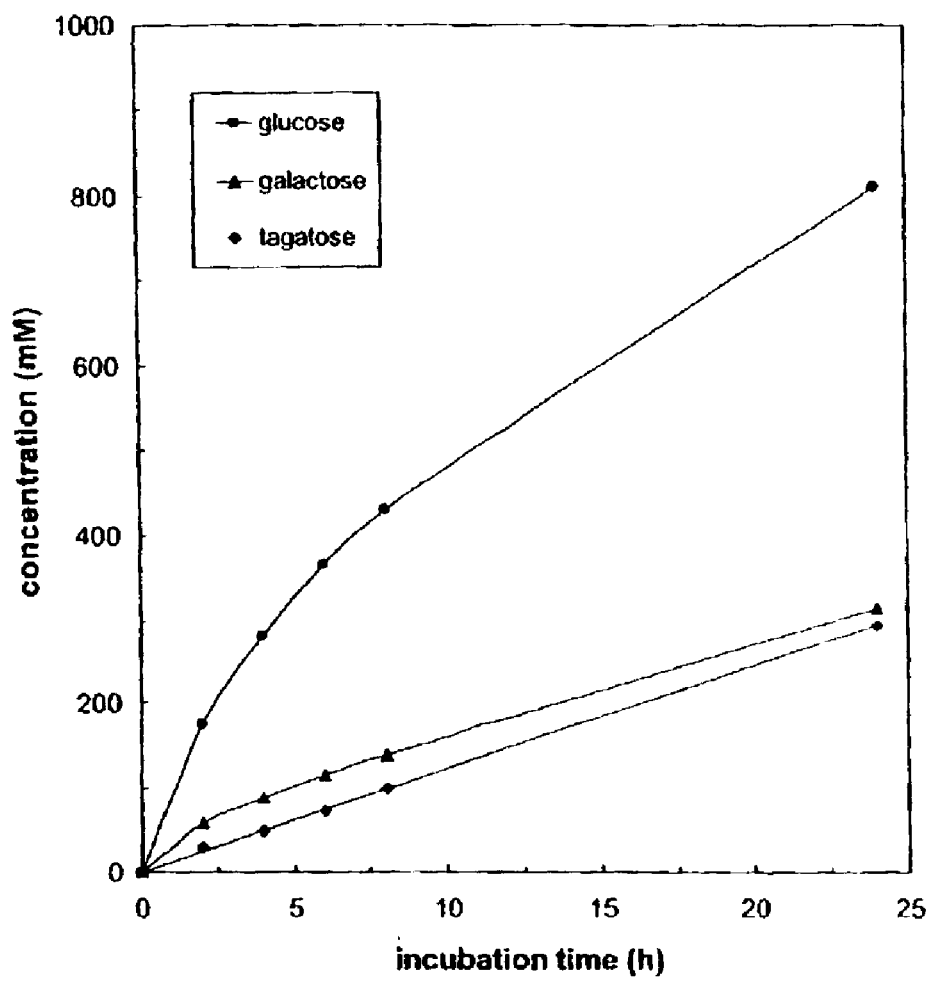

The invention is further illustrated in the following, non-limiting examples and the drawings, wherein FIG. 1 is a genetic map of the DNA fragment from *T. mathranii* which was cloned in *E. coli*, as described in Example 1, FIG. 2 shows the percentage of identical amino acid residues found by pairwise alignment of a number of known araA sequences as compared to the sequence from *T. mathranii*. The known sequences are identified by EMBL/Genbank database accession numbers, FIG. 3 shows a phylogenetic tree based on all the L-arabinose isomerase amino acid sequences presently available in public sequence databases and the sequence from *T. mathranii*, FIG. 4 shows an amino acid sequence alignment of the araA gene from *Thermoanaerobacter mathranii* and other araA sequences presently available in public databases. The numbers shown below the sequences refer to the araA sequence from *T. mathranii*. The catalytically active amino acid residues in the active site of the *E. coli* L-fucose isomerase are Glu337 and Asp361, and the putative corresponding amino acids are marked with a "#" in the alignment of L-arabinose isomerase sequences. Conserved amino acid residues are marked with a "*", conservative substitutions are marked with a ":", and related residues are marked with a ".". The alignment was made with the program CLUSTAL X (1.8), FIG. 5 illustrates the temperature dependence of L-arabinose isomerase from *T. mathranii* produced in *E. coli*, FIG. 6 illustrates the pH dependence of L-arabinose isomerase from *T mathranii* produced in *E. coli*, and FIG. 7 illustrates the single-reactor conversion of lactose to tagatose with immobilised lactase and immobilised isomerase.

EXAMPLE 1

Cloning of the L-arabinose Isomerase Gene (araA) from *Thermoanaerobacter mathranii* and Heterologous Production of the Enzyme in *E. coli*

The anaerobic, thermophilic microorganism *Thermoanaerobacter mathranii* DSMZ 11426 was obtained from Deutsche Sammlung von Mikroorganismen und Zellkulturen GmbH, Mascheroder Weg 1b, D-38124 Braunschweig, Germany (DSMZ). Originally, the strain was described as "strain A3" (Sonne-Hansen, J., Mathrani, I. M. and Ahring, B. K. (1993) *Appl. Microbiol. Biotechnol.* 38: 537–541). Later, the strain was deposited at DSMZ and the name *T. mathranii* was proposed (Larsen, L., Nielsen, P. and Ahring, B. (1997) *Arch. Microbiol.* 168: 114–119).

1.1. Growth of *T. mathranii*

*T. mathranii* (DSMZ 11426) was cultivated at 65° C. under anaerobic conditions in the medium recommended by DSMZ. After growth, the culture was centrifuged and the pellet was stored at −80° C. until purification of chromosomal DNA.

1.2. Gene Cloning

A standard phenol/chloroform extraction method described by Sambrook et al was used for purification of total chromosomal DNA from frozen *T. mathranii* cells. Purified chromosomal DNA was partially cleaved with Sau3A restriction enzyme (New England Biolabs) and DNA fragments of about 3–4 kb were purified from agarose gels using the GFX Gel Band Purification kit (Amersham Pharmacia Biotech).

The pBluescript KS(+/−) plasmid (Stratagene Cloning Systems) was cleaved with BamHI restriction enzyme (New England Biolabs), treated with alkaline phosphatase (CIP, New England Biolabs) and purified from agarose gels using the GFX Gel Band Purification kit (Amersham Pharmacia Biotech). After ligation of purified DNA fragments and purified plasmid vector, the ligation mixture was introduced into super competent DH10B cells (Life Technologies) by electroporation as described by the manufacturer. Transformed cells were plated onto LB medium containing ampicillin (100 µg/ml). About 16,000 colonies were pooled from 20 plates, and a Jetstar kit (Genomed) was used to make a plasmid preparation from the pooled cells.

The plasmid library prepared from pooled cells was introduced by electroporation into UP1089 cells, an *Escherichia coli* strain carrying an araA mutation that prevents it from growing on an L-arabinose minimal medium. The UP1089 strain was purchased from *E. coli* Genetic Stock Center, 355 Osborn Memorial Laboratories, Department of Biology, P.O. Box 208104, Yale University, New Haven, Conn. 06520–8104, USA. After transformation with the plasmid library, the UP1089 cells were plated onto minimal medium containing L-arabinose as the only sugar, thus selecting for complementation of the araA mutation. About 90 colonies were obtained by selection for growth on L-arabinose minimal medium plates.

1.3. DNA Sequencing and Phylogenetic Comparison

Plasmid inserts from two of these colonies were selected for DNA sequencing (ALF Express, Amersham Pharmacia Biotech), and they were found to contain identical DNA fragments comprising an L-arabinose isomerase gene (araA) followed by an L-ribulokinase gene (araB) (FIG. 1). The nucleotide sequence of the 5'-part of a cloned DNA fragment comprising the araA and araB genes is shown in the below Table 1 1. The open reading frame of the araA gene is shown in bold

TABLE 1.1

Nucleotide sequence of DNA fragment comprising the *araA* and *araB* genes of *Thermoanaerobacter matrahnii*

(SEQ ID NO:1)

```
GATCTATTAA ACGGTGTGTG TGTAATAGAG ACAGAGGCAG AACGAGAAGA TTATGGGTCA TGGGGAGAAG ACCTTTATAA     90

GGTAGATGTT AATGTATCGT ATAAGCCCGT GAGAATAAAA TTTATACCGT ATTTTGCATG GGCGAACCGT GCACCGGGTG    160

AAATGATGGT ATGGGTAAGG GAAAAGTAAA ATTACTAGAA GGGGTTTTAA TGTGTTTAAT CAAGAAGGTA GAAATATAGG    240

TTTAAATGGC AAAGGAACAA GTTTTTGTAT ATTGATAAAG TATATAAAAC CTAAGATAGT TTTATATTTA TTTGTCTAAG    320

TTTTAGAAAT AAATTTTTTA AAAACAAAGA ACGAATTTTG AATAAAATGT AGAATATATT AATTATAAAT GTACGTACAT    400

CTAATATCAT GATAATTAAA ATATACGAAC AACAAAATAA CAAATCAAAA GGAGGATTTA TTATGCAAAC CAAGAAAAAG    480

CCGCAAATAG GATTTTTAGG CATTATGCAA GAGTTGTACG ATGATATGTT ACCAGGCATT ACTGAAAGAC AAGAAAAATA    560

TGCAAGAGAA GTTATAGAAC AACTTCAAGA TGTTGCCGAT TTTCATTTTC CTAAAGCAGC AAAGAATAGA CAGGACATTG    640

AACATATTGT GAAAGAATTT AATGAAAAAG ACCTTGATGG TATTATGATA GTAATGCTTA CGTATGGACC TGCTACAAAT    720

ATTGTTAATG CACTAAGGAA TAATAAACTA CCTATTATGC TTGCCAACAT TCAACCTGTT CCGACAGTAA CAGAGGATTC    800

GGATATGGGA GATTTGACAT ACAATCAAGG TGTTCACGGT GCCCAAGATA CAGCAAATGC CATTTTAAGG ATGGGAATTA    880

AGTGTCCTAT TATTACAGAA GAATGGCATT CAGAAGAATT TAAAAAATTT GTTGGAGATT GGGCTAAAGC TGTGCAGACA    960

ATTAAAGCAT TGCGAAACAT GAAAATAGCG CAGTTTGGAA GAATGCATGG AATGTATGAT ATTTTGGGAG ATGATGCAGC   1040

CTTTACAAGA AAAATAGGTC CGCAAATTAA TCAAGAATAC ATTGGCGAAG TTTATAGATA TATGGAAACT GCGACAGAAG   1120

AGGAGATTAA TGCGGTTATT GAAGAGAATA GAAAGAATTT TTATATCGAT CCAAATCTTA GCCAAGAAAG CCATAGATAT   1200

GCTGCAAGAT TACAAATTGG ATTTAAAAAA TTTCTTATTA ATAAAGGATA TGACGGATTT ACTGCGCATT TCGATGTGTT   1280

TAAAGGAGAT GGAAGATTCA AGCAAATTCC AATGATGGCT GCGTCAAATT TAATGGCTGA AGGATATGGA TATGCAGCAG   1360

AGGGTGATGC TGTAACTGCA AGTTTGGTTG CGGCAGGTCA TGTATTGATA GGAGATGCAC ATTTTACTGA GATGTACGCT   1440

ATGGATTTTA AGAGAAATTC AATTTTAATG AGCCATATGG GCGAAGGTAA CTGGAAAATA GCAAGAAAGG ATAGACCGAT   1520

TAAACTTATT GATAGAGAAC TGGGCATTGG AAAACTTGAT AATCCGCCGA CAATTGTGTT TATGGCACAA CCTGGGCCAG   1600

CAACTCTTGT TTCTTTAGTA TCCTTAGAAG GAGAAAGATA TAGGTTAGTT GTGTCAAAAG GAGAAATTCT GGATACAGAA   1680
```

TABLE 1.1-continued

Nucleotide sequence of DNA fragment comprising the araA and araB genes of
Thermoanaerobacter matrahnii

| | | | | | | |
|---|---|---|---|---|---|---|
| GAAGCAAAGT | ATATTGAAAT | GCCATATTTC | CACTTTAGAC | CTTCAACAGG | TGTGAAGGCA | TGTCTTGATG GATGGCTTAC 1760 |
| AAATGGAGGA | ACACATCATG | AATGTTTAAA | TCTAGGTGAT | AACACACGGA | GATGGAAAAT | ATTATGTAAC CTCTTGGACA 1840 |
| TTGAATATGT | AGAAGTATAG | GGGGATGAAA | AATGGCAAAG | TATTCAATTG | GAATAGATTA | CGGGACAGAC TCTGCAAGGG 1920 |
| CTCTGCTCCT | TAATCTTGAG | ACGGGAGAAG | AAGTAGCTAC | TTCTGTAATG | AATTATCCCC | ATGGCGTGAT GGATGAAGAA 2000 |
| CTTCCTGATG | GAACAAAACT | TCCACAAGAT | TGGGCATTAC | AACATCCAGA | TGACTATATT | GAAGTTTTAA AGAAAATAGT 2080 |
| ACCTGATGTA | ATAAATCAGG | CAGGTATAGA | CAAAGCTGAT | GTAATAGGCT | TAGGCATAGA | TTTTACAGCT TGTACTATGT 2160 |
| TGCCTATAAA | AAAAGATGGA | ACTCCTCTTT | GTGACATCCC | CCAGTACAAA | TCGAACCCTC | ATTCATATGT TAAGTTATGG 2240 |
| AAACATCATG | CTGCGCAACC | TGAAGCAAAC | AAATTGAATG | AAATAGCATC | ACAAAGGGGT | GAGGATTTTT TAGCAAGGTA 2320 |
| TGGAGGAAAA | ATATCTTCAG | AATGGCTCAT | ACCCAAAATA | TGGCAAATAT | TAAATGAAGC | GCCAGATATC TATCAAGAAG 2400 |
| CTGATAAATT | TATTGAAGCT | ACTGATTGGG | TTGTTATGAA | GCTAACAGGT | AATGAAAGGC | GAAATAGCTG TACTGCAGCC 2480 |
| TATAAAGCGA | TTTGGCACAA | AGAAAGGGG | TATCCTTCCA | AAGATTTCTT | TCGAGCATTA | GATGAGAGGC TTCAAAATTT 2560 |
| GGTAGAAGAA | AAATTATCTA | AAGATATATA | TCCATTAGGT | ACAAAAGCAG | GGGAATTGAC | GCCTGAAATG GCAAAAATAT 2640 |
| TGGGCTTAAA | CCCGGGAGTA | GCGGTTGCTG | TAGGCAATGT | TGATGCTCAT | GTTTCAGTAC | CAGCAGTAGG AGTTACATCG 2720 |
| CCAGGGAAAA | TGGTAATGGT | AATGGGAACT | TCGATTTGCC | ATTTGGTGTT | AGATGATAAA | GAAGTAGAGG TCCCAGGCAT 2800 |
| GTGTGGCGTT | GTAGAAGATG | GAATTATACC | AGGCTTTTAT | GGATATGAAG | CAGGACAATC | TGCGGTTGGC GACATCTTTG 2880 |
| CCTGGTTTGT | TGATAATTGT | GTGCCGTACG | AATACAAAAT | TGAAGCAGAA | AAAGAGGGA | TAAGTATTCA CGAGTTATTA 2960 |
| ACAGAAAAAG | CCGCAAAGCT | AAAACCCGGA | GAAAGTGGCC | TCTTGGCGAT | TGACTGGTGG | AACGGAAACA GGTCAGTACT 3040 |
| AGTAGATGCA | GACCTTACTG | GTGTAATATT | AGGAATGACT | TTAACTACGA | AACCTGAGGA | GATATACAGA GCATTAATCG 3120 |
| AAGCAACAGC | TTTTGGGACG | AGGATGATAA | TTGATACTTT | TAATCAAAAT | GCAGTAAGTA | TTAGTGAACT CTACGCTTGT 3200 |
| GGAGGACTTC | CTGAAAAAAA | TCCTATGCTT | ATGCAAATCT | ATGCTGATGT | TACAAATCTC | GAAATTAAAG TATCAAAATC 3280 |
| TTCACAAACA | CCAGCACTTG | GTGCAGCAAT | GTTTGGAGCA | GTTGCAGCAG | GTAAAGCAAA | AGCAGGGTTT GATAGTATAT 3360 |
| TTGAAGCGGC | ACGAGTAATA | CCCAAGCTAA | AGGAAGAAAC | ATACAATCCA | ATACCTGAAA | ATGTTGAAAT ATATGATAAA 3410 |
| TTATTTGAAG | AATACAAACT | TCTTCATGAC | TATTTTGGCA | GAGGTATAAA | TAATGTAATG | AAAAGGCTAA AAGCCTTAAA 3520 |
| AGAGGGGGTT | TCCAATGTTA | GAGAAGCTTA | AAGAACGAGT | ATACAAAATG | AATATGATGT | TGCCGAAAAA TAATCTTGTT 3600 |
| ACAATGACAA | GTGGGAATGT | CAGTGGAAGA | GATGTTGAAA | CAGGATATGT | AGTTATAAAA | CCAAGCGGGA TTCCTTATGA 3680 |
| AGAAATGCAA | CCAGAGGATA | TGGTTGTGGT | TGACCTTAA | | | 3719 |

The open reading frame of the araA gene encoded 465 amino acid residues, corresponding to a molecular weight of 52,785 Da. The amino acid sequence of the AraA gene product (SEQ ID NO:2) deduced from the sequence of Table 1.1 is shown in the below Table 1.2.

TABLE 1.2

Amino acid sequence of ArA gene product of T. mathranii DSMZ 11426

| | | | | | |
|---|---|---|---|---|---|
| MQTKKKPQIG | FLGIMQELYD | DMLPGITERQ | ERYAREVIEQ | LQDVADFHFP | 50 (SEQ ID NO:2) |
| KAAKNRQDIE | HIVKEFNEKD | LDGIMIVMLT | YGPATNIVNA | LRNNKLPIML | 100 |
| ANIQPVPTVT | EDWDMGDLTY | NQGVHGAQDT | ANAILRMGIK | CPIITEEWHS | 150 |
| EEFKKFVGDW | AKAVQTIKAL | RNMKIAQFGR | MHGMYDILGD | DAAFTRKIGP | 200 |
| QINQEYIGEV | YRYMETATEE | EINAVIEENR | KNFYIDPNLS | EESHRYAARL | 250 |
| QIGFKKFLIN | KGYDGFTAHF | DVFKGDGRFK | QIPMMAASNL | MAEGYGYAAE | 300 |

TABLE 1.2-continued

Amino acid sequence of ArA gene product of *T. mathranii* DSMZ 11426

```
GDAVTASLVA AGHVLIGDAH FTEMYAMDFK RNSILMSHMG EGNWKIARKD 350

RPIKLIDREL GIGKLDNPPT IVFMAQPGPA TLVSLVSLEG ERYRLVVSKG 400

EILDTEEAKY IEMPYFHFRP STGVKACLDG WLTNGGTHHE CLNLGDNTRR 450

WKILCNLLDI EYVEV                                      465
```

The amino acid sequence showed homology to previously known L-arabinose isomerases. The percentage of identical amino acid residues was relatively low, 24–30%, when the *T. mathranii* sequence was aligned with other araA genes (FIG. 4). In comparison, the identity level was above 46% within the reference group of previously known L-arabinose isomerases (FIG. 2). The L-arabinose isomerase amino acid sequences presently available in public sequence databases and the sequence from *T. mathranii* were subsequently used for construction of a phylogenetic tree (FIG. 3) using the ClustalX program (Thompson, J D., Gibson, T. J., Plewniak, F., Jeanmougin, F. and Higgins, D. G. (1997) *Nucleic Acids Res.* 25: 4876–4882).

One of the two colonies was selected for further use.

1.4. Heterologous Production of *T. mathranii* L-arabinose Isomerase in *E. coli* UP1089 Cells

*E. coli* cells harbouring the L-arabinose isomerase gene were grown over night at 37° C. in LB medium containing ampicillin (100 μg/ml). After centrifugation, the cells were resuspended in 50 mM Tris-Cl, pH 7.5 and lysed in a French pressure cell operated at 1100 psig Cell debris was removed by centrifugation and the resulting cell extract was used for characterisation of the enzyme, as described below.

EXAMPLE 2

Characterisation of L-arabinose Isomerase from *T. mathrani* Produced in *E. coli*

5 2.1. Assay Method

L-arabinose isomerase activity was determined as described by Yamanaka, K. and Wood, W. A. (1966) *Methods in Enzymology* 9: 596–602. Enzyme sample, 10–50 μl, was mixed with 950 μl of assay reagent and incubated at 65° C. for 60 min. The final concentrations were: L-arabinose, 5 mM; MnCl$_2$, 5 mM; maleate buffer, pH 6.9, 25 mM. When galactose or fucose was used as a substrate, the concentration of D-galactose or D-fucose was 0.5 M and the incubation time was about 16 h.

The obtained concentrations of the ketoses L-ribulose, D-tagatose or D-fuculose, respectively, were determined by the cysteine-carbazol-sulfuric acid method (Dische, Z. and Borenfreund, E. (1951) *J. Biol. Chem.* 192: 583–587). Samples were incubated at room temperature for 60 min and the absorbance at 560 nm was measured in a microplate reader. Standard curves showing the colour response of 0–5 mM ketose were made with D-tagatose and D-ribulose, since L-ribulose was not commercially available. (No standard curve was obtained for D-fuculose which was not commercially available.)

The concentrations of lactose, D-glucose, D-galactose, D-tagatose, L-ribulose and D-fuculose were determined by high pressure liquid chromatography using an Aminex HPX-87C column (Bio-Rad) and a refractive index detector. The mobile phase was de-ionised, degassed water, the column temperature was 85° C., and the flow rate was 0.6 ml/min.

2.2. Temperature Dependence

D-galactose assays performed at increasing temperatures between 45° C. and 85° C. showed highest activity at 65° C. (FIG. 5).

2.3. pH Dependence

D-galactose assays performed at pH 4, 5, 6, 7, 8 and 9, respectively showed highest activity at pH 8 (FIG. 6). The buffer used for these assays was a mixture of 25 mM acetic acid, 25 mM 2-[N-morpholino]ethanesulfonic acid (MES), 5 mM MnCl$_2$, and 25 mM tris[hydroxymethyl]-aminomethane (TRIS), which was titrated with HCl or NaOH.

2.4. Metal Ion Requirement

A range of metal salts (MnCl$_2$, NaCl, KCl, MgSO$_4$, ZnSO$_4$, CuSO$_4$, and FeSO$_4$) were tested for their ability to reactivate enzyme which had previously been dialysed against a buffer containing 5 mM ethylenediaminetetraacetic acid (EDTA) Only addition of MnCl$_2$ (100%) or FeSO$_4$ (76%) restored the L-arabinose isomerase activity.

Other L-arabinose isomerase enzymes from *Escherichia coli* (Patrick, J. W. and Lee, N (1968) *J. Biol. Chem.* 243: 4312–4318), *Aerobacter aerogenes* (Yamanaka, K. and Wood, W. A. (1966) *Methods in Enzymology* 9: 596–602), and *Lactobacillus gayonii* (Nakamatu, T. and Yamanaka, K. (1968) *Biochim. Biophys. Acta* 178: 156–165) have also been reported to require Mn$^{2+}$.

2.5. Molecular Weight

A native molecular weight of about 220 kDa was determined by gel filtration on a Super-dex 200 HR10/30 column (Amersham Pharmacia Biotech) and enzyme assay of collected fractions.

Sodium dodecyl sulphate polyacrylamide gel electrophoresis (SDS-PAGE) of collected fractions showed a subunit molecular weight of about 55 kDa, which is in good agreement with the subunit size of 53 kDa predicted from the DNA sequence of the araA open reading frame (465 amino acid residues). The identity of the 55-kDa L-arabinose isomerase band seen in SDS-PAGE was verified by electrophoretic transfer of the polypeptide to polyvinylidene difluoride (PVDF) membrane and N-terminal amino acid sequencing in an automated microsequencer. The N-terminal sequence, MQTKKK-, was identical to the amino acid sequence deduced from the DNA sequence of the araA gene from *T. mathranii*, as described above in Example 1.

The observed native molecular weight of about 220 kDa and the subunit size of about 55 kDa suggest that the active enzyme is a tetramer. The corresponding enzyme in *E. coli* is a hexamer containing six identical subunits of about 60 kDa (Patrick, J. W. and Lee, N. J. (1969) *J. Biol. Chem.* 244: 4277–4283).

2.6. Substrate Specificity

It has been reported previously that certain L-arabinose isomerase enzymes may isomerise not only L-arabinose, but also D-galactose and D-fucose (Yamanaka, K. and Wood, W. A. (1966) *Methods in Enzymology* 9: 596–602). These sugars have the same configuration ration at $C_1$ to $C_4$, including an L-cis configuration at $C_2$–$C_3$.

The molar ratio of keto-sugar generated by isomerisation of L-arabinose and D-galactose respectively, was determined at a substrate concentration of 0.5 M (pH 6.9, 65° C.). The ratio was calculated from the cysteine-carbazol-sulfuric acid colour responses and the standard curves generated with ribulose and tagatose, respectively. This calculation showed that the D-galactose activity was 21% of the L-arabinose activity.

The colour response obtained with 0.5 M D-fucose was 46% of the corresponding response seen with L-arabinose. The molar ratio between the D-fucose and L-arabinose activity could not be calculated, since no standard curve was obtained for D-fuculose No significant enzyme activity was detected with other aldo-hexoses (D-glucose, D-mannose), other aldo-pentoses (D-arabinose, L-ribose, D-ribose, D-xylose), or with another deoxy-sugar (L-fucose).

2.7. Substrate Affinity

The apparent Michaelis-Menten constants, $K_m$ of the enzyme were about 80 mM for L-arabinose, about 120 mM for D-galactose, and about 145 mM for D-fucose. Previously reported values for other L-arabinose isomerases are shown in Table 2.1. The broad substrate specificity shown above and the similar $K_m$ values for L-arabinose, D-galactose, and D-fucose suggest that the enzyme of the invention, compared to other L-arabinose isomerases, is a versatile aldose isomerase which is capable of isomerising a range of structurally related aldoses.

TABLE 2.1

Substrate affinity of L-arabinose isomerases: $K_m$ values for L-arabinose, D-galactose and D-fucose

| Origin of enzyme | Reference | L-arabinose | D-galactose | D-fucose |
|---|---|---|---|---|
| *T. mathranii* (produced in *E. coli*) | this work | ~80 mM | ~120 mM | ~145 mM |
| *Aerobacter aerogenes* | 1 | 33 mM | 370 mM | 270 mM |
| *Bacillus amyloliquefaciens* | 2 | | 670 mM | |
| *Arthrobacter sp.* | 2 | | 870 mM | |
| *Lactobacillus pentosus* | 2 | | 1110 mM | |
| *Escherichia coli* | 3 | 60 mM | | |
| *Lactobacillus plantarum* | 4 | 28 mM | | |
| *Lactobacillus gayonii* | 5 | 55 mM | | |
| *Mycobacterium smegmatis* | 6 | ~30 mM | | |

References Cited in Table 2.1:
1: Yamanaka, K. and Wood, W. A. (1966) *Methods in Enzymology* 9: 596–602
2: Ibrahim, O. O. and Spradlin, J. E., U.S. Pat. No. 6,057,135 (Kraft Foods, Inc.)
3: Patrick, J. W. and Lee, N. (1968) *J. Biol. Chem* 243: 4312–4318
4: Heath, E. C., Horecker, B. L., Smyrniotis, P. Z. and Takagi, Y. (1958) *J. Biol. Chem.* 231:1031–1037
5: Nakamatu, T and Yamanaka, K. (1969) *Biochim. Biophys. Acta* 178: 156–165
6: Izumon, K., Yeda, Y. and Yamanaka, K. (1978) *J. Bacteriol.* 133: 413–414

2.8. Enzymatic Bioconversion of D-galactose to D-tagatose with Non-immobilised Enzyme Free enzyme was used to demonstrate the bioconversion potential of the enzyme at elevated substrate concentrations. One-ml assay mixtures containing 0.20 ml of *E. coli* cell extract with recombinant L-arabinose isomerase from *T. mathranii*, 0.30 g of D-galactose (30%, 1.67 M) or 0.60 g of D-galactose (60%, 3.33 M), 25 mM maleate buffer, pH 6.9 and 5 mM $MnCl_2$ were incubated at 65° C. Control samples without enzyme were treated similarly. Periodically, samples were taken and the concentration of D-tagatose was determined by the cystein-carbazol-sulfuric acid method as described above. The results are shown in Table 2.2A (30% D-galactose) and 2.2B (60% D-galactose).

TABLE 2.2A

Bioconversion of D-galactose to D-tagatose with free enzyme Initial conc. of D-galactose 30% (1.67 M)

| Incubation time (h) | Conc. of D-tagatose (mM) | Percent bioconversion |
|---|---|---|
| 0 | 0 | 0 |
| 24 | 427 | 25 |
| 48 | 450 | 26 |
| 72 | 422 | 25 |

TABLE 2.2B

Bioconversion of D-galactose to D-tagatose with free enzyme Initial concentration of D-galactose 60% (3.33 M)

| Incubation time (h) | Conc. of D-tagatose (mM) | Percent bioconversion |
|---|---|---|
| 0 | 0 | 0 |
| 24 | 462 | 14 |
| 48 | 542 | 16 |
| 72 | 622 | 19 |

EXAMPLE 3

Bioconversion of D-galactose to D-tagatose with Immobilised Enzyme 3.1 Enzyme Immobilisation by Cross-linking with Glutaraldehyde and Polyethylenimine Cells from a 2-liter culture of *E. coli* cells producing L-arabinose isomerase were collected by centrifugation and homogenised in a French Pressure Cell as described above. The enzyme was immobilised by cross-linking all cell components with glutaraldehyde and polyethylenimine as described in U.S. Pat. No. 4,355,105. Glutaraldehyde, 25% (w/v), was obtained from Merck, Darmstadt, Germany and polyethylenimine, 50% (w/v), was obtained from Sigma Chemicals. The cross-linked enzyme was recovered by centrifugation, and the pellet was lyophilised and stored at 4° C. until further use.

The activity of the immobilised enzyme was determined by incubation of 20 mg of freeze-dried enzyme in a one-ml assay mixture containing 0.30 g of D-galactose (30%, 1.67 M), 25 mM maleate buffer, pH 6.9 and 5 mM $MnCl_2$ at 65° C. A control sample without enzyme was treated similarly. Periodically, samples were taken and the concentration of D-tagatose was determined by high-pressure liquid chromatography. The yield of immobilised enzyme was generally 60–100 units per liter of *E. coli* cell culture, and the recovery of enzyme activity after immobilisation was about 50%. The specific activity of the immobilised enzyme preparation was about 55 units per gram freeze-dried enzyme. One unit was defined as the amount of enzyme producing one micromole of D-tagatose per min at 65° C., pH 6.9, in a 30% (w/v) solution of D-galactose.

3.2. Enzymatic Bioconversion of D-galactose to D-tagatose with Cross-linked, Immobilised Enzyme One-ml assay mixtures containing 40 mg of freeze-dried enzyme (2.2 units), 0.30 g of D-galactose (30%, 1.67 M), 25 mM maleate buffer, pH 6.9 and 5 mM $MnCl_2$ were incubated at 65° C. A control sample without enzyme was treated similarly. Periodically, samples were taken and the concentration of D-tagatose was determined by high pressure liquid chromatography. The results are shown in Table 3.1.

TABLE 3.1

Bioconversion of D-galactose to D-tagatose with cross-linked, immobilised enzyme

| Incubation time (h) | Concentration of D-tagatose (mM) | Percent bioconversion[a] |
|---|---|---|
| 0 | 0 | 0 |
| 2 | 182 | 11 |
| 4 | 249 | 15 |
| 6 | 317 | 19 |
| 24 | 593 | 36 |
| 48 | 700 | 42 |

[a]The inital concentration of galactose was 30% (w/v) corresponding to 1.67 M

3.3. Long-term Stability of the Immobilised Enzyme

A sample of freeze-dried enzyme (40 mg, 2.2 units) was incubated at 65° C. in a one-ml assay mixture containing 0.30 g of D-galactose (30%, 1.67 M), 25 mM maleate buffer, pH 6.9 and 5 mM $MnCl_2$. Samples for determination of the concentration of D-tagatose were taken at 0 h and 24 h and analysed by HPLC as described above. After sampling at 24 h the sugar solution above the immobilised enzyme was removed, and fresh assay solution was added to a final volume of 1.0 ml. The 24-h incubation was repeated four times using the same enzyme sample for all the galactose-to-tagatose conversion cycles The final concentration of tagatose after conversion for 24 h remained constant (average 529 mM±5%) during repeated bioconversions with the same enzyme sample (Table 3.2), and even after operation for more than 100 h at 65° C. the enzyme showed no sign of a reduced reaction rate. The experiment demonstrated that the immobilised enzyme is a stable bio-catalyst which may be used for multiple, repeated bioconversions of galactose to tagatose.

TABLE 3.2

Long-term stability of the immobilised enzyme

| Cycle no. | Time (h) | Tagatose conc. (mM) | Tagatose production during 24 h (mM) |
|---|---|---|---|
| 1 | 0 | 0 | 524 |
|   | 24 | 524 |   |
| 2 | 24 | 165* | 339 |
|   | 48 | 504 |   |
| 3 | 48 | 148* | 408 |
|   | 72 | 556 |   |
| 4 | 72 | 153* | 364 |
|   | 96 | 517 |   |
| 5 | 96 | 142* | 400 |
|   | 120 | 542 |   |

*The concentration of tagatose determined at the beginning of cycles 2, 3, 4 and 5 originated from dilution of the tagatose found in the residual assay solution surrounding the immobilised enzyme after the preceding 24-h incubation.

EXAMPLE 4

Single-reactor Conversion of Lactose to Tagatose with Immobilised Lactase and Immobilised Isomerase The combined use of a thermostable, immobilised lactase and a thermostable immobilised L-arabinose isomerase for direct, high-temperature conversion of lactose to tagatose in a single reactor was demonstrated. The enzyme selected for lactose hydrolysis was the extremely thermostable β-glycosidase from the thermoacidophilic archaeon *Sulfolobus solfataricus* (Moracci, M., Ciaramella, M. and Rossi, M. [2001] Methods in Enzymology 330: 201–15). This broad-spectrum enzyme is an efficient lactose, and it has successfully been cloned and expressed in *E. coli* and other microbial host organisms (ibid.).

While most of the previously characterised lactases are strongly inhibited by galactose, this particular enzyme has been reported not to be inhibited by galactose, and to be only moderately inhibited by glucose (Pisani, F. M., Rella, R., Raia, C. A., Rozzo, C., Nucci, R., Gambacorta, A., De Rosa, M. and Rossi, M. [19901] Eur J Biochem. 187;321–328). Pisani et al 1990). These favourable properties with regard to end-product inhibition were expected to be highly advantageous for hydrolysis of lactose at a high substrate concentration such as 30% (w/v). Furthermore, the *S. solfataricus* enzyme requires no cofactor, unlike, for example, the β-galactosidase from *E. coli* which is $Mg^2$, dependent. Therefore, only the cofactor required by the *T. mathranii* isomerase, manganese ions, had to be included in the reaction medium, thus excluding any influence from a cofactor required by the lactase.

4.1. Heterologous Production in *E. coli* and Immobilisation of β-glycosidase from *Sulfolobus solfataricus*

The β-glycosidase encoding gene from *Sulfolobus solfataricus* was cloned and expressed in *E. coli*. The gene was isolated by polymerase chain reaction (PCR) using purified chromosomal DNA from *Sulfolobus solfataricus* strain P2. Primers containing additional restriction sites for NdeI and BamHI were designed to yield the entire coding sequence on a fragment which was subsequently cloned into the standard expression plasmid pET3a (Novagen).

*E. coli* cells producing the enzyme were cultivated, harvested by centrifugation, lysed in a French pressure cell and cross-linked with glutaraldehyde and polyethylenimine as described in U.S. Pat. No. 4,354,105. The immobilised enzyme was recovered by centrifugation and lyophilisation of the pellet. The activity of the immobilised lactase was 1500 units/g dry weight. One unit was defined as the amount of enzyme liberating one micromole of glucose per min at 65° C., pH 6.5, in a 30% (w/v) solution of lactose.

4.2. Heterologous Production in *E. coli* and Immobilisation of L-arabinose Isomerase from *Thermoanaerobacter mathranii*

L-arabinose isomerase from *Thermoanaerobacter mathranii* was produced in *E. coli* and immobilised as described above in Example 3.1.

4.3. Single-reactor Conversion of Lactose to Tagatose with Immobilised Lactase from *S. solfataricus* and Immobilised L-arabinose Isomerase from *T. mathranii*

One-ml assay mixtures containing 20 mg (30 units) of immobilised lactase, 80 mg (4.4 units) of immobilised isomerase, 0.30 g of lactose (30%, 875 mM), 25 mM K-maleate buffer, pH 6.9, and 5 mM $MnCl_2$ were incubated at 65° C. A control sample without enzymes was treated similarly. Periodically, samples were taken and the concentrations of glucose, galactose and tagatose were determined by high pressure liquid chromatography. As shown in FIG. 7, the concentration of glucose increased to about 800 mM over 24 h, indicating that almost all lactose was hydrolysed to galactose and glucose The concentration of tagatose increased linearly to about 300 mM over 24 h, indicating a bioconversion of about 38% (300 mM/800 mM).

The successful hydrolysis of lactose and the subsequent isomerisation of galactose to tagatose demonstrated that the two enzymes involved were able to operate under the same reaction conditions with regard to pH, temperature, buffer components and metal-ion concentration (5 mM $MnCl_2$). In addition, it was demonstrated that the isomerase enzyme is unaffected by the high concentration of glucose present as a result of the lactose hydrolysis.

REFERENCES

Altschul, S. F., Gish, W., Miller, W., Myers, E. W. and Lipman, D. J. (1990) *J. Mol. Biol.* 215:403–10

Dische, Z. and Borenfreund, E (1951) *J. Biol. Chem.* 192: 583–587

Heath, E. C., Horecker, B. L., Smyrniotis, P. Z. and Takagi, Y. (1958) *J. Biol. Chem.* 231: 1031–1037

Izumori, K., Yeda, Y. and Yamanaka, K. (1978) *J. Bacteriol.* 133: 413–414

Larsen, L., Nielsen, P. and Ahring, B. (1997) *Arch. Microbiol.* 168. 114–119

Nakamatu, T. and Yamanaka, K. (1969) *Biochim. Biophys. Acta* 178: 156–165

Patrick, J. W. and Lee, N (1968) *J. Biol. Chem.* 243: 4312–4318

Patrick, J. W. and Lee, N. J. (1969) *J. Biol. Chem.* 244: 4277–4283

Pisani, F. M., Rella, R., Raia, C. A., Rozzo, C., Nucci, R., Gambacorta, A., De Rosa, M. and Rossi, M. (1990) *Eur J Biochem.* 187:321–328

Moracci, M., Ciaramella, M. and Rossi, M. (2001) *Methods in Enzymology* 330: 201–15

Sambrook, J., Fritsch, E. F. and Maniatis, T. Molecular cloning: A Laboratory Manual, second edition (1989) Cold Spring Harbor Laboratory, Cold Spring Harbor, N.Y., USA Seemann, J. E. and Schulz, G. E. (1997) *J. Mol. Biol.* 273:256–68

Sonne-Hansen, J., Mathrani, I. M. and Ahring, B. K. (1993) *Appl. Microbiol. Biotechnol.* 38: 637–541

Thompson, J. D., Gibson, T. J., Plewniak, F., Jeanmougin, F. and Higgins, D. G (1997) *Nucleic Acids Res.* 25: 4876–4882

Yamanaka, K. and Wood, W. A. (1966) *Methods in Enzymology* 9: 596–602

What is claimed is:

1. An L-arabinose isomerase capable of isomerizing D-galactose to D-tagatose, which isomerase has at least 90% sequence identity to the sequence of SEQ ID NO:2.

2. The isomerase of claim 1 having the amino sequence of SEQ ID NO: 2.

3. A method of converting an aldose into a ketose comprising contacting the aldose with the isomerase of claim 1 and keeping the reaction under conditions where at least 1% by weight of the aldose is converted.

4. The method of claim 3 wherein the aldose is selected from the group consisting of L-arabinose, D-galactose and D-fucose.

5. The method of claim 3 wherein the reaction takes place at a temperature of at least 60° C.

6. The method of claim 3 wherein at least 10% by weight of the substrate aldose is converted to its corresponding ketose.

7. The method of claim 6 wherein at least 25% by weight of the substrate aldose is converted into its corresponding ketose.

8. The method of claim 6 wherein the ketose is D-tagatose.

9. The method of claim 3 wherein the L-arabinose isomerase is provided as an isolated enzyme preparation.

10. The method of claim 3 wherein the isolated enzyme preparation is immobilised.

11. The method of claim 3, further comprising the step of hydrolysing lactose to obtain D-galactose by use of a lactase-active enzyme, wherein D-galactose is converted to D-tagatose.

12. The method of claim 11 wherein the lactase is immobilised and the isomerase enzyme preparation is immobilized, and wherein the lactose hydrolysation and the aldose isomerisation takes place in the same reactor.

13. The method of claim 11 wherein the lactase-active enzyme is β-glycosidase.

14. A method of converting D-galactose into D-tagatose comprising contacting the D-galactose with the isomerase of claim 1 and keeping the reaction under conditions where at least 1% by weight of the D-galactose is converted.

15. A composition comprising the isomerase of claim 1 in an immobilised form.

* * * * *